(12) United States Patent
Kovacic et al.

(10) Patent No.: US 10,449,516 B2
(45) Date of Patent: Oct. 22, 2019

(54) SUPERABSORBENT POLYMERIC STRUCTURES

(71) Applicant: Technion Research & Development Foundation Limited, Haifa (IL)

(72) Inventors: Sebastijan Kovacic, Haifa (IL); Michael S. Silverstein, Zikhron-Yaakov (IL)

(73) Assignee: Technion Research & Development Foundation Limited, Haifa (IL)

( * ) Notice: Subject to any disclaimer, the term of this patent is extended or adjusted under 35 U.S.C. 154(b) by 20 days.

(21) Appl. No.: 15/595,970

(22) Filed: May 16, 2017

(65) Prior Publication Data

US 2017/0326529 A1 Nov. 16, 2017

(30) Foreign Application Priority Data

May 16, 2016 (IL) .......................................... 245656

(51) Int. Cl.

| | | |
|---|---|---|
| *A61L 15/24* | (2006.01) | |
| *A61L 15/42* | (2006.01) | |
| *A61L 15/60* | (2006.01) | |
| *B01J 20/26* | (2006.01) | |
| *B01J 20/28* | (2006.01) | |
| *B01J 20/30* | (2006.01) | |
| *C08F 120/70* | (2006.01) | |
| *C08J 3/075* | (2006.01) | |
| *C08J 9/28* | (2006.01) | |
| *C09J 133/26* | (2006.01) | |

(52) U.S. Cl.
CPC ............ *B01J 20/267* (2013.01); *A61L 15/24* (2013.01); *A61L 15/425* (2013.01); *A61L 15/60* (2013.01); *B01J 20/28045* (2013.01); *B01J 20/3071* (2013.01); *C08F 120/70* (2013.01); *C08J 3/075* (2013.01); *C08J 9/28* (2013.01); *C08J 9/283* (2013.01); *C09J 133/26* (2013.01); *C08J 2201/026* (2013.01); *C08J 2201/028* (2013.01); *C08J 2201/05* (2013.01); *C08J 2205/022* (2013.01); *C08J 2205/05* (2013.01); *C08J 2333/26* (2013.01)

(58) Field of Classification Search
CPC ................ B01J 20/267; B01J 20/28045; B01J 20/3071; C08J 3/075; C08J 2333/26; C08J 9/28; C08J 9/283; C08J 2201/026; C08J 2201/028; C08J 2201/05; C08J 2205/05; A61L 15/24; A61L 15/425; A61L 15/60

See application file for complete search history.

(56) References Cited

U.S. PATENT DOCUMENTS

| | | |
|---|---|---|
| 2,801,185 A | 7/1957 | Iler |
| 3,417,171 A | 12/1968 | Eberle et al. |
| 4,455,205 A | 6/1984 | Olson et al. |
| 4,478,876 A | 10/1984 | Chung |
| 4,486,504 A | 12/1984 | Chung |
| 4,491,508 A | 1/1985 | Olson et al. |
| 4,522,958 A | 6/1985 | Das et al. |
| 5,258,225 A | 11/1993 | Katsamberis |
| 5,648,407 A | 7/1997 | Goetz et al. |
| 5,652,194 A | 7/1997 | Dyer et al. |
| 6,147,131 A | 11/2000 | Mork et al. |
| 6,204,298 B1 | 3/2001 | DesMarais et al. |
| 6,241,713 B1 | 6/2001 | Gross et al. |
| 6,353,037 B1 | 3/2002 | Thunhorst et al. |
| 6,573,305 B1 | 6/2003 | Thunhorst et al. |
| 6,586,483 B2 | 7/2003 | Kolb et al. |
| 7,129,277 B2 | 10/2006 | Baran, Jr. |
| 7,189,768 B2 | 3/2007 | Baran, Jr. et al. |
| 7,507,780 B2 | 3/2009 | Hagerty et al. |
| 7,967,367 B2 | 6/2011 | Cafeo et al. |
| 2002/0091368 A1* | 7/2002 | LaVon .............. A61F 13/15203 604/385.14 |
| 2003/0097103 A1 | 5/2003 | Horney et al. |
| 2003/0170308 A1* | 9/2003 | Cleary .................... A61L 15/60 424/486 |
| 2004/0204510 A1 | 10/2004 | Clear et al. |
| 2004/0224021 A1 | 11/2004 | Omidian et al. |
| 2009/0215913 A1 | 8/2009 | Thies et al. |
| 2009/0270538 A1* | 10/2009 | Ikeuchi ..................... C08F 2/44 524/115 |
| 2012/0201806 A1 | 8/2012 | Silverstein et al. |
| 2012/0261803 A1 | 10/2012 | Wang et al. |
| 2013/0324627 A1 | 12/2013 | Silverstein et al. |
| 2014/0011897 A1 | 1/2014 | Friederichs et al. |
| 2014/0328884 A1 | 11/2014 | Reyes et al. |
| 2015/0166753 A1 | 6/2015 | Silverstein et al. |
| 2016/0287516 A1 | 10/2016 | Cosgriff-Hernandez et al. |

(Continued)

FOREIGN PATENT DOCUMENTS

| | | |
|---|---|---|
| CA | 2322498 | 9/1999 |
| CN | 107126936 | 9/2017 |

(Continued)

OTHER PUBLICATIONS

Office Action dated Dec. 28, 2017 From the Israel Patent Office Re. Application No. 253431. (4 Pages).
International Search Report and the Written Opinion dated Nov. 12, 2017 From the International Searching Authority Re. Application No. PCT/IL2017/050904. (13 Pages).
Office Action dated Feb. 8, 2018 From the Israeli Patent Office Re. Application No. 247302 and Its Translation Into English. (11 Pages).
International Search Report and the Written Opinion dated Sep. 27, 2017 From the International Searching Authority Re. Application No. PCT/IL2017/050706. (17 Pages).

(Continued)

*Primary Examiner* — Melissa A Rioja

(57) ABSTRACT

Provided herein is a superabsorbent polyHIPE composition-of-matter comprising a majority of ionizable pendant groups, capable of absorbing up to 300-fold by mass water while exhibiting a notable mechanical strength in both the dry and wet form, as well as various uses thereof.

20 Claims, 8 Drawing Sheets

(56) References Cited

U.S. PATENT DOCUMENTS

| | | |
|---|---|---|
| 2017/0189238 A1 | 7/2017 | Andrews |
| 2019/0127546 A1 | 5/2019 | Silverstein et al. |

FOREIGN PATENT DOCUMENTS

| | | |
|---|---|---|
| WO | WO 94/12134 | 6/1994 |
| WO | WO 02/008321 | 1/2002 |
| WO | WO 2009/013500 | 1/2009 |
| WO | WO 2015/076908 | 5/2015 |
| WO | WO 2018/002916 | 1/2018 |
| WO | WO 2018/002916 A8 | 1/2018 |
| WO | WO 2018/033913 | 2/2018 |
| WO | WO 2018/033913 A8 | 2/2018 |
| WO | WO 2019/012529 | 1/2019 |
| WO | WO 2019/016816 | 1/2019 |
| WO | WO 2019/087185 | 5/2019 |

OTHER PUBLICATIONS

Notice of Omitted Item(s) in a Nonprovisional Application dated Jan. 8, 2015 From the US Patent and Trademark Office Re. U.S. Appl. No. 14/578,519.
Office Action and Search Report dated Mar. 1, 2017 From the Israel Patent Office Re. Application No. 247302. (7 Pages).
Office Action and Search Report dated Dec. 4, 2016 From the Israel Patent Office Re. Application No. 245656. (7 Pages).
Office Action and Search Report dated Mar. 16, 2017 From the Israel Patent Office Re. Application No. 246468. (8 Pages).
Office Action dated Sep. 7, 2017 From the Israel Patent Office Re. Application No. 247302 and Its Translation Into English. (12 Pages).
Office Action dated Jul. 16, 2017 From the Israel Patent Office Re. Application No. 245656 and Its Translation Into English. (4 Pages).
Office Action dated Nov. 16, 2016 From the Israel Patent Office Re. Application No. 246468. (2 Pages).
Office Action dated Jun. 21, 2016 From the Israel Patent Office Re. Application No. 245656. (3 Pages).
Office Action dated May 23, 2016 From the Israel Patent Office Re. Application No. 245656. (2 Pages).
Office Action dated Sep. 25, 2016 From the Israel Patent Office Re. Application No. 247302. (1 Page).
Office Action dated Sep. 28, 2017 From the Israel Patent Office Re. Application No. 246468 and Its Translation Into English. (6 Pages).
Official Action dated Sep. 5, 2014 From the US Patent and Trademark Office Re. U.S. Appl. No. 13/369,362.
Official Action dated Oct. 6, 2015 From the US Patent and Trademark Office Re. U.S. Appl. No. 14/578,519.
Official Action dated May 13, 2014 From the US Patent and Trademark Office Re. U.S. Appl. No. 13/892,606.
Restriction Official Action dated Feb. 12, 2014 From the US Patent and Trademark Office Re. U.S. Appl. No. 13/892,606.
Audouin et al. "Preparation, Solid-State NMR, and Physicochemical Characterization of Surprisingly Tough Open Cell PolyHIPEs Derived From 1-Vinyl-1,2,4-Triazole Oil-in-Water Emulsions", Macromolecules, 44(12): 4879-4886, May 27, 2011.
Audouin et al. "Synthesis of Porous Materials by 2-Nitroresorcinol/ Cyanuric Chloride Thermal Polycondensation in Emulsions", Journal of Applied Polymer Science, 108(5): 280802813, Published Online Feb. 25, 2008.
Barbetta et al. "High Internal Phase Emulsions (HIPEs) Containing Divinylbenzene and 4-Venylbenzyl Chloride and the Morphology of the Resulting PolyHIPE Materials", Chemical Communications, p. 221-222, 2000.
Chung et al. "The Thermoresponsive Shape Memory Characteristics of Polyurethane Foam", Journal of Applied Polymer Science, 117: 2265-2271, 2010.
Cohen Samoocha "Bicontinuous Hydrogel-Filled Hydrophobic Polymers Synthesized Within Polymer-Nanoparticle-Stabilized Pickering Emulsions", M.Sc. Thesis, Department of Materials Science and Engineering, Abstract. Apr. 2015.
Colver et al. "Cellular Polymer Monoliths Made Via Pickering High Internal Phase Emulsions", Chemical Materials, 19: 1537-1539, 2007.
David et al. "Porous Polyurethanes Synthesized Within High Internal Phase Emulsions", Journal of Polymer Science Part A: Polymer Chemistry, 47(21): 5806-5814, Sep. 28, 2009. Abstract, Fig.3, p. 5807-5808, p. 5809, Line 2, 5813.
Deleuze et al. "Preparation and Functionalisation of Emulsion-Derived Microcellular Polymeric Foams (PolyHIPEs) by Ring-Opening Metathesis Polymerisation (ROMP)", Chemistry Communications, 2002(23): 2822-2823, Advance Publication Oct. 25, 2002.
Gitli et al. "Emulsion Templated Bicontinuous Hydrophobic-Hydrophilic Polymers: Loading and Release", Polymer, 52(1): 107-115, Available Online Nov. 13, 2010.
Gurevitch et al. "Nanoparticle-Based and Organic-Phase-Based AGET ATRP PolyHIPE Synthesis Within Pickering HIPEs and Surfactants-Stabilized HIPEs", Macromolecules, 44(9): 3398-3409, Apr. 15, 2011.
Gurevitch et al. "Polymerized Pickering HIPEs: Effects of Synthesis Parameters on Porous Structure", Journal of Polymer Science, Part A: Polymer Chemistry, 48: 1516-1525, 2010.
Ikem et al. "High Internal Phase Emulsions Stabilized Solely by Functionalized Silica Particles", Angewandte Chemie, International Edition, 47: 8277-8279, 2008.
Kapilov-Buchman et al. "Water-Filled Elastomers Through Droplet Microencapsulation: Release and Degradation", Department of Materials Science and Engineering, Technion—Israel Institute of Technology, Haifa, Israel, Poster, Dec. 31, 2015.
Kapilov-Buchman et al. "Water-Filled Elastomers Through Droplet Microencapsulation: Release and Degradation", Presentation in the Conference IMEC, BarIlan University, Israel, Feb. 1-2, 2016, 17 P., Feb. 2, 2016.
Kovacic et al. "Macroporous Double Network Hydrogels Through Emulsion Templating", Presented at the Polymer Chemistry Gordon Research Conference, Poster, Jun. 30, 2015.
Luo et al. "One-Pot Interfacial Polymerization to Prepare PolyHIPEs With Functional Surface", Colloid and Polymer Science, 293(6): 1767-1779, Published Online Mar. 25, 2015.
M?lhaupt "Catalytic Polymerization and Post Polymerization Catalysis Fifty Years After the Discover of Ziegler's Catalysts", Macromolecular Chemistry and Physics, 204(2): 289-327, Feb. 2003.
Madhusudhana et al. "Bicontinuous Highly Cross-Linked Poly(Acrylamide-Co-Ethyleneglycol Dimethacrylate) Porous Materials Synthesized Within High Internal Phase Emulsions", Soft Matter, 7: 10780-10786, Sep. 28, 2011, p. 10781, Left Col., Lines 11-15, PolyHIPES Synthesis Section, p. 10782, Left Col., Lines 28-37, p. 10785, Right Col., Lines 5-8, p. 10786, Left Col., Lines 3-5.
Menner et al. "High Internal Phase Emulsion Templates Solely Stabilised by Functionalised Titania Nanoparticles", Chemical Communications, p. 4274-4276, 2007.
Menner et al. "Particle-Stabilized Surfactant-Free Medium Internal Phase Emulsions as Templates for Porous Nanocomposite Materials: Poly-Pickering-Foams", Langmuir, 23: 2398-2403, 2007.
Oh et al. "Injectable, Interconnected, High-Porosity Macroporous Biocompatible Gelatin Scaffolds Made by Surfactant-Free Emulsion Templating", Macromolecular Rapid Communications, 36(4): 364-372, Published Online Dec. 10, 2014.
Silverstein "Emulsion-Templated Porous Polymers: A Retrospective Perspective", Polymer, 55(1): 304-320, Available Online Sep. 11, 2013.
Silverstein et al. "PolyHIPEs—Porous Polymers From High Internal Phase Emulsions", Encyclopedia of Polymer Science and Technology, p. 1-24, 2010.
Streifel et al. "Porosity Control in High Internal Phase Emulsion Templated Polyelectrolytes Via Ionic Crosslinking", Journal of Polymer Science, Part A: Polymer Chemistry, 54(16): 2486-2492, Published Online Apr. 13, 2016.

(56) References Cited

OTHER PUBLICATIONS

Tobushi et al. "The Influence of Shape-Holding Conditions on Shape Recovery of Polyurethane-Shape Memory Polymer Foams", Smart Materials and Structures, 13: 881-887, 2005.
Unknown "Salt Solution-Filled Elastomeric Monoliths Through Templating Within Pickering Emulsions: Release and Degradation", 1 P., Jul. 2016.
Yakacki et al. "Strong, Tailored, Biocompatible Shape-Memory Polymer Networks", Advanced Functional Materials, 18(16): 2428-2435, Aug. 22, 2008.
Zhang et al. "PMMA Based Foams Made Via Surfactant-Free High Internal Phase Emulsion Templates", Chemical Communications, p. 2217-2219, 2009.
Zhou et al. "Ion-Responsive Alginate Based Macroporous Injectable Hydrogel Scaffolds Prepared by Emulsion Templating", Journal of Materials Chemistry B: Materials for Biology and Medicine, 1(37): 4736-4745, Oct. 7, 2013.
Zhu et al. "Monolithic Supermacroporous Hydrogel Prepared From High Internal Phase Emulsions (HIPEs) for Fast Removal of Cu2+ and Pb2+", Chemical Engineering Journal, 284: 422-430, Available Online Sep. 9, 2015.
Office Action dated Aug. 30, 2018 From the Israel Patent Office Re. Application No. 247302 and Its Translation Into English. (13 Pages).
Office Action dated Feb. 8, 2018 From the Israel Patent Office Re. Application No. 246468 and Its Translation Into English. (4 Pages).
Office Action and Search Report dated Mar. 11, 2018 From the Israel Patent Office Re. Application No. 255404. (7 Pages).
Kabiri et al. "Novel Sulfobetaine-Sulfonic Acid-Contained Superswelling Hydrogels", Polymers for Advanced Technologies, 16(9): 659-666, Published Online Aug. 4, 2005.
Lalani et al. "Electrospun Zwitterionic Poly(Sulfobetaine Methacrylate) for Nonadherent, Superabsothent, and Antimicrobial Wound Dressing Applications", Biomacromolecules, 13(6): 1853-1863, Apr. 30, 2012.
Laschewsky "Structures and Synthesis of Zwitterionic Polymers", Polymers, 6(5): 1544-1601, May 23, 2014.
Maji et al. "Dual-Stimuli-Responsive L-Serine-Based Zwitterionic UCST-Type Polymer With Tunable Thermosensitivity", Macromolecules, 48(14): 4957-4966, Jul. 20, 2015.
Tan et al. "Synthesis and Aqueous Solution Properties of Sterically Stabilized PH-Responsive Polyampholyte Microgels", Journal of Colloid and Interface Science, 309: 453-463, Available Online Feb. 16, 2007.
Office Action and Search Report dated Sep. 5, 2018 From the Israel Patent Office Re. Application No. 256783. (14 Pages).
International Preliminary Report on Patentability dated Jan. 10, 2019 From the International Bureau of WIPO Re. Application No. PCT/IL2017/050706. (10 Pages).
International Search Report and the Written Opinion dated Jan. 27, 2019 From the International Searching Authority Re. Application No. PCT/IL2018/051158. (12 Pages).
Zhang et al. "Highly Porous, Emulsion-Templated, Zwitterionic Hydrogels: Amplified and Accelerated Uptakes With Enhanced Environmental Sensitivity", Polymer Chemistry, 9(25): 3479-3487, Published Online May 21, 2018.
International Search Report and the Written Opinion dated Nov. 1, 2018 From the International Searching Authority Re. Application No. PCT/IL2018/050803. (11 Pages).
International Search Report and the Written Opinion dated Nov. 20, 2018 From the International Searching Authority Re. Application No. PCT/IL2018/050751. (15 Pages).
Kovačič et al. "Superabsorbent, High Porosity, PAMPS-Based Hydrogels Through Emulsion Templating", Macromolecular Rapid Communications, 37(22): 1814-1819, Sep. 2016.
Zhang et al. "Doubly-Crosslinked, Emulsion-Templated Hydrogels Through Reversible Metal Coordination", Polymer, 126: 386-394, Jul. 18, 2017. Esp. Sections 2.2-2.4, Section 3.9.
Zheng et al. "Metal-Coordination Complexes Mediated Physical Hydrogels with High Toughness, Stick—Slip Tearing Behavior, and Good Processability", Macromolecules, 49(24), 9637-9646, Dec. 2016.
International Preliminary Report on Patentability dated Feb. 28, 2019 From the International Bureau of WIPO Re. Application No. PCT/IL2017/050904. (8 Pages).

* cited by examiner

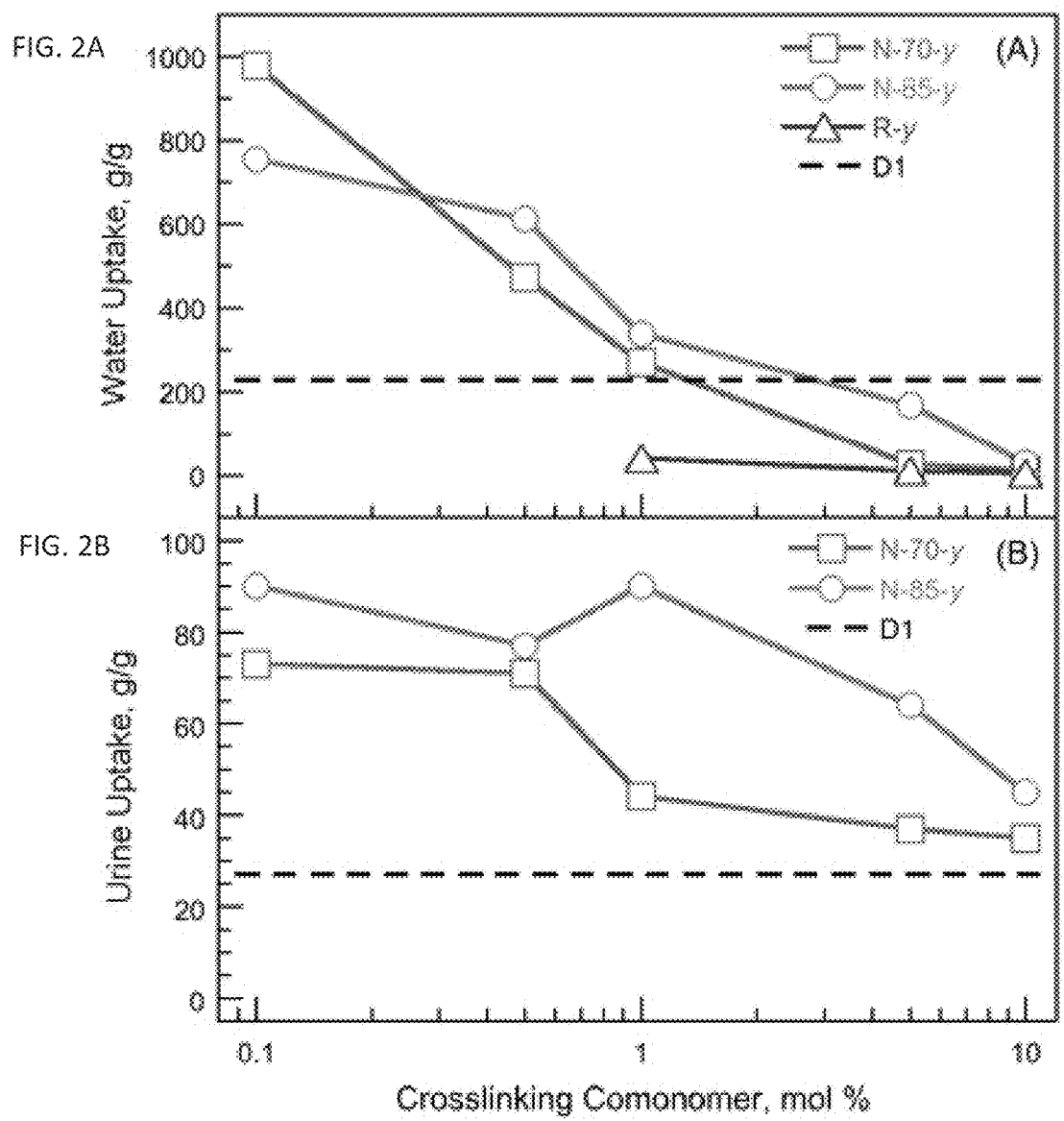

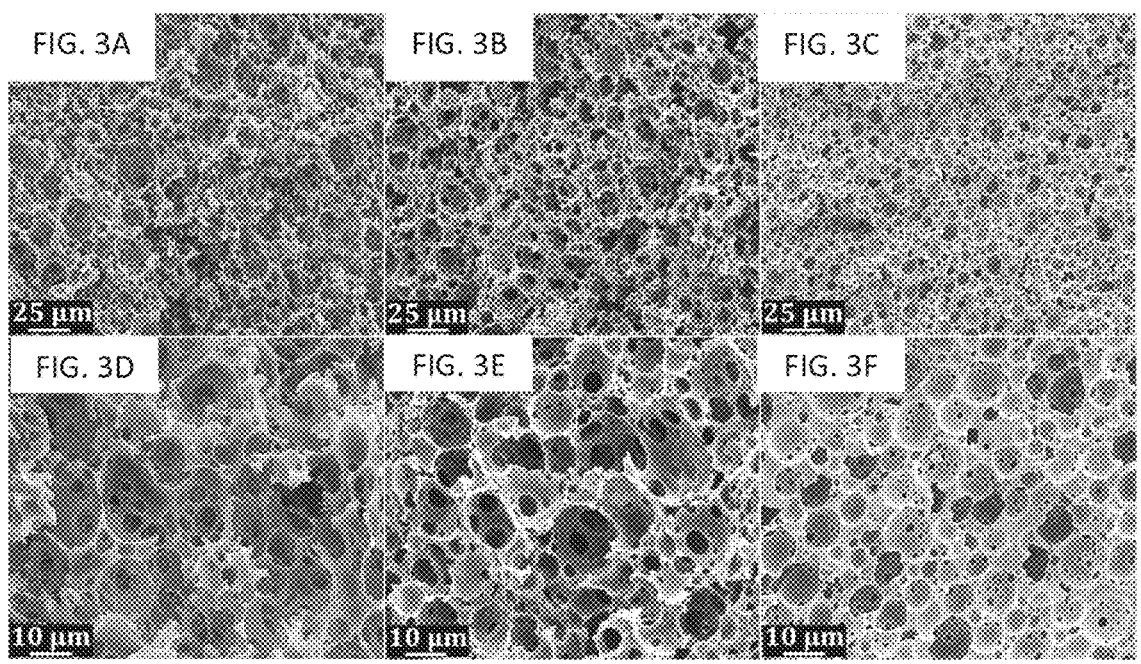

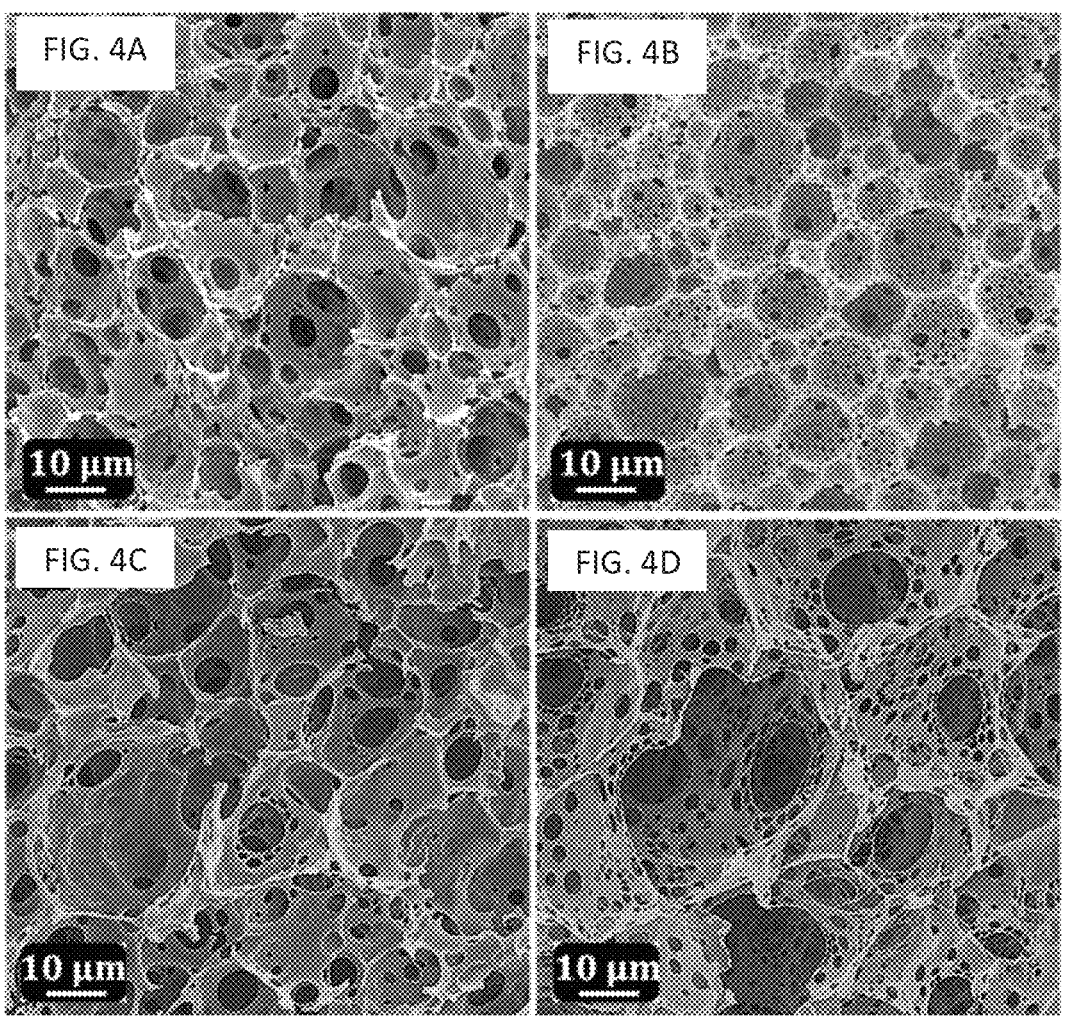

SUPERABSORBENT POLYMERIC STRUCTURES

RELATED APPLICATION

This application claims the benefit of priority of Israel Patent Application No. 245656 filed on May 16, 2016, the contents of which are incorporated herein by reference in their entirety.

FIELD AND BACKGROUND OF THE INVENTION

The present invention, in some embodiments thereof, relates to material science, and more particularly, but not exclusively, to superabsorbent polymeric hydrogels and uses thereof.

Superabsorbent polymers are polymers that can absorb and retain extremely large amounts of a liquid relative to their own mass. When crosslinked and soaked with aqueous media (such as water), superabsorbent polymers are referred to as hydrogels that may absorb 800 times their dry weight and swell up to 100 times of their dry volume, to constitute up to 99.9% liquid. The total absorbency and swelling capacity are controlled by the type and degree of crosslinking of the polymer.

Superabsorbent crosslinked polymers are used commercially since 1970's in personal disposable hygiene products, diapers, sanitary napkins, blocking water penetration, horticultural water retention, spill and waste control, and even for making artificial snow.

The most common commercially-used superabsorbent polymers typically comprise polymerized alkaline acrylic acid that forms sodium polyacrylate. Other materials used for superabsorbent polymer include polyacrylamide copolymer, ethylene maleic anhydride copolymer, cross-linked carboxymethylcellulose, polyvinyl alcohol copolymers, cross-linked polyethylene oxide, and starch-grafted copolymer of polyacrylonitrile.

Presently known superabsorbent hydrogels are usually mechanically fragile in both the dry and swollen state, and most of these release the absorbed water when put under stress/pressure. To mitigate these problems, a number of relatively tougher hydrogels have been developed, some based on nanocomposite hydrogels that incorporate clay, and others based on double-network gels that combine a densely crosslinked ionic hydrogel with a lightly crosslinked non-ionic hydrogel. However, the increase in toughness often comes at the expense of water-uptake capacity.

Cipriano, B. H. et al., [Macromolecules, 2014, 47(13), pp 4445-4452] reported a superabsorbent hydrogels having superior mechanical properties based on self-crosslinking N,N-dimethylacrylamide (DMAA) and sodium acrylate.

High internal phase emulsions (HIPEs) are typically formed from two immiscible liquids, typically being water as a major dispersed or internal phase, and a highly hydrophobic liquid as a minor continuous or external phase. PolyHIPEs are highly porous polymeric structures formed by polymerization of monomers within the external phase of HIPEs. Thus, polyHIPEs are high internal phase emulsion-templated polymeric structures having highly interconnected porous microstructures. The microstructure of a polyHIPE consists primarily of large spheroidal voids, which are the structural remnants of the internal phase droplets, connected by "windows" where adjacent droplets were in close proximity. The size and shape of the voids are conferred by the droplets, and may be tens to hundreds of micrometers in diameter, whereas the interconnecting windows are in the hundreds to thousands of nanometers in diameter. For a review, see Feuerabendt, F. et al. [*IJERR*, 2014, 2(1), pp. 23-31].

Absorbent foams made from polyHIPEs are disclosed, for example, in U.S. Pat. Nos. 4,522,953, 5,550,167, 5,571,849, 5,633,291, 5,692,939, 5,728,743, 5,753,359, 5,770,634, 6,013,589, 6,048,908, 6,083,211, 6,147,131, 6,207,724, 6,362,243, 6,444,716, 6,525,106, 7,820,729, 8,921,435, 9,062,245 and 9,180,094.

Foams made from hydrophobic polyHIPEs are polymeric structures templated by water-in-oil (w/o) HIPEs. The water absorption expected in such hydrophobic polyHIPEs, typically characterized by porosities of 80 to 90%, is about 8 to 9 g/g (gram water to gram polymer).

Hydrophilic polyHIPE foams are polymeric structures templated by oil-in-water (o/w) HIPEs. Oil-in-water HIPEs comprising only ionic polymers (derived from ionic monomers) are difficult to stabilize through the polymerization process, and thus a compromise between pre-polymerization stability and pre-polymerization monomer composition restricts the hydrophilic polyHIPE available to date.

Krajnc and co-workers reported an oil-in-water HIPE consisting of acrylic acid, water, and a crosslinker (N,N'-methylene bisacrylamide) as the water phase, and toluene as the oil phase, which was successfully stabilized to sustain thermal initiation of radical polymerization to afford a porous open-cell monolithic material [Krajnc, P. et al., *Macromol. Rapid Commun.*, 2005, 26, pp. 1289-1293]. This work was silent with respect to water absorption or mechanical properties of the resulting reticulated and highly porous foams.

Hydrophilic polyHIPE hydrogels based on a pre-polymerization mixture of non-ionic monomers, such as hydroxyethyl methacrylate (HEMA), and ionic monomers, such as methacrylic acid (MAA), were recently reported as having water absorption capacities of up to 18 g/g [Ovadia, M. and Silverstein, M. S., *Polymer International*, 2016, 65(3), pp. 280-289]. This unusually high water absorption was attributed to absorption that fills the original voids, swells the hydrogel walls, and fills the volume generated by hydrogel-swelling-driven void expansion.

SUMMARY OF THE INVENTION

A high capacity high durability superabsorbent polymeric structure, designed to sustain form and hold liquid under compressive strain, comprising strongly hydratable and highly accessible pendant groups assembled in a microstructure of a polyHIPE is provided herein.

According to an aspect of some embodiments of the present invention there is provided a composition-of-matter that includes a crosslinked polymer, the composition-of-matter is having a microstructure of a polymerized external phase of a high internal phase emulsion (HIPE) and characterized by a dry density that ranges from 0.05 g/cm$^3$ to 0.4 g/cm$^3$, wherein:

a crosslinking level of the crosslinked polymer ranges from 0.1 to 15 mol percent; and the crosslinked polymer is having a plurality of pendant groups, at least a portion of which are ionizable pendant groups that are more strongly hydrated than a carboxylic pendant group;

such that the composition-of-matter is characterized by:

an equilibrium aqueous medium absorption of at least 8 g/g; and a compressive failure strain at of at least 25% when the composition-of-matter is fully swollen with the aqueous medium.

According to some embodiments of the invention, the strain at fail of the composition-of-matter is at least 2-fold greater than a compressive failure strain of a bulk of the crosslinked polymer of a similar size and shape.

According to some embodiments of the invention, the ratio of the ionizable pendant groups to non-ionizable pendant groups in the crosslinked polymer is greater than 85 percent.

According to some embodiments of the invention, the ratio is greater than 95 percent.

According to some embodiments of the invention, the polymer is substantially devoid of non-ionizable pendant groups.

According to some embodiments of the invention, the ionizable pendant groups comprise at least one organosulfur group.

According to some embodiments of the invention, the organosulfur group is selected from the group consisting of sulfonate and sulfate.

According to some embodiments of the invention, the organosulfur group is sulfonate.

According to some embodiments of the invention, the microstructure is an open-cell microstructure.

According to some embodiments of the invention, the crosslinked polymer that includes poly(2-acrylamido-2-methylpropanesulfonic acid).

According to some embodiments of the invention, the polymer is crosslinked with N,N'-methylenebisacrylamide (MBAAm).

According to some embodiments of the invention, the crosslinking level is 0.1% and the dry density is 0.15 g/cm$^3$.

According to some embodiments of the invention, the crosslinking level is 0.5% and the dry density is 0.15 g/cm$^3$.

According to some embodiments of the invention, the crosslinking level is 1% and the dry density is 0.15 g/cm$^3$.

According to some embodiments of the invention, the crosslinking level is 5% and the dry density is 0.15 g/cm$^3$.

According to some embodiments of the invention, the crosslinking level is 10% and the dry density is 0.15 g/cm$^3$.

According to some embodiments of the invention, the crosslinking level is 0.1% and the dry density is 0.30 g/cm$^3$.

According to some embodiments of the invention, the crosslinking level is 0.5% and the dry density is 0.30 g/cm$^3$.

According to some embodiments of the invention, the crosslinking level is 1% and the dry density is 0.30 g/cm$^3$.

According to some embodiments of the invention, the crosslinking level is 5% and the dry density is 0.30 g/cm$^3$.

According to some embodiments of the invention, the crosslinking level is 10% and the dry density is 0.30 g/cm$^3$.

According to some embodiments of the invention, the HIPE includes an organic internal phase and an aqueous external phase, the aqueous external phase being a pre-polymerization mixture that includes a plurality of monomers and crosslinking agents, wherein a mol percent of the crosslinking agents in the plurality of monomers and crosslinking agents ranges from 0.1 percent to 15 percent, and the internal phase constitutes from 60 percent to 95 percent of the HIPE.

According to some embodiments of the invention, least 85 percent of the plurality of monomers include an ionizable monomer.

According to some embodiments of the invention, the ionizable monomer is selected from the group consisting of 2-acrylamido-2-methylpropane sulfonic acid (AMPS), 2-acrylamido-2-propanesulfonic acid, 1-acrylamido-1-propanesulfonic acid, 2-(methacryloyloxy)ethanesulfonic acid, 2-hydroxy-3-(2-propenyloxy)-propanesulfonic acid, 2-methacrylamido-2-methyl-1-propanesulfonic acid, 2-methyl-2-propene-1-sulfonic acid, 2-propene-1-sulfonic acid, 2-sulfoethyl acrylate, 2-sulfoethyl methacrylate, 3-methacrylamido-2-hydroxypropanesulfonic acid, 3-sulfopropyl acrylate, 3-sulfopropyl methacrylate, 3-sulfopropylacrylate, 3-sulfopropylmethacyrlate, allyl sulfonic acid, allyloxybenzenesulfonic acid, methallyloxybenzenesulfonic acid, methallylsulfonic acid, phenylethenesulfonic acid, styrenesulfonic acid, sulfomethacrylamide, sulfomethylmethacrylamide, vinylsulfonic acid, and any salts thereof, and any combinations thereof.

According to some embodiments of the invention, the ionizable monomer is 2-acrylamido-2-methylpropane sulfonic acid.

According to some embodiments of the invention, the crosslinking agent is selected from the group consisting of N,N'-methylenebisacrylamide (MBAAm) ethylene glycol diacrylate, diethylene glycol diacrylate, N-(1-hydroxy-2,2-dimethoxyethyl)acrylamide, N,N'-(1,2-Dihydroxyethylene) bisacrylamide, and any combination thereof.

According to some embodiments of the invention, the crosslinking agent is N,N'-methylenebisacrylamide.

According to some embodiments of the invention, the organic internal phase comprises toluene.

According to some embodiments of the invention, the HIPE further includes a surfactant and an initiator.

According to some embodiments of the invention, the surfactant is a hydrophilic non-ionic surfactant.

According to some embodiments of the invention, the surfactant is selected from the group consisting of a poloxamer, an alkylphenol hydroxypolyethylene and a polyethoxylated sorbitan ester.

According to some embodiments of the invention, the surfactant is selected from the group consisting of Poloxamer 407, Triton X-405, Triton X-100, Triton X-705 and Tween 20.

According to some embodiments of the invention, the surfactant is Poloxamer 407.

According to some embodiments of the invention, the amount of the surfactant in the HIPE ranges from 2 to 6 percent by weight of the aqueous external phase.

According to an aspect of some embodiments of the present invention there is provided a hydrogel that includes the composition-of-matter presented herein and an aqueous medium absorbed therein.

According to some embodiments of the invention, the aqueous medium is water, a solution of a water-soluble substance, waste-water, and urine.

According to an aspect of some embodiments of the present invention there is provided an article of manufacturing that includes the composition-of-matter presented herein.

According to some embodiments of the invention, the article of manufacturing is selected from the group consisting of a diaper, an incontinence garment, a fire-retardant material, a flood/spill control device, a fragrance carrier, thermal pack, a liquid waste device, an ion-exchange matrix, a filter matrix, a water purification matrix, a surgical pad, a water retention device, a cosmetic product, a personal hygiene product, a personal care product, a grooming product and a wound dressing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrase "substantially devoid of" or "essentially devoid of" a certain substance refers to a composition that is totally devoid of this substance or includes no more than about 1, 0.5 or 0.1 percent of the substance by weight or volume.

The term "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is expected that during the life of a patent maturing from this application many relevant HIPE-templated superabsorbent hydrogel structures will be developed and the scope of the phrase "HIPE-templated superabsorbent hydrogel structures" is intended to include all such new technologies a priori.

BRIEF DESCRIPTION OF THE SEVERAL VIEWS OF THE DRAWINGS

Some embodiments of the invention are herein described, by way of example only, with reference to the accompanying drawings or images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-B present comparative plot of water uptake (FIG. 2A), and urine uptake (FIG. 2B), as a function of crosslinker level (0.1, 0.5, 1, 5 and 10 molar percent) on a logarithmic scale, as observed in exemplary compositions-of-matter, according to some embodiments of the present invention (N-70-y marked by squares and N-85-y marked by circles), their corresponding reference bulk hydrogels (marked by triangles), and a superabsorbent polymer used in commercial disposable household diapers (D1; dashed line);

FIGS. 3A-F present SEM micrographs of exemplary dry compositions-of-matter, according to some embodiments of the present invention, wherein FIG. 3A is of dry N-70-1, FIG. 3B is of dry N-70-5, FIG. 3C is of dry N-70-10, FIG. 3D is of dry N-85-1, FIG. 3E is of dry N-85-5, and FIG. 3F is of dry N-85-10;

FIGS. 4A-D present SEM micrographs of exemplary compositions-of-matter, according to some embodiments of the present invention, wherein FIG. 4A shows the microstructure of a dry N-70-5 sample before it has been exposed to water, FIG. 4B shows the microstructure of a dry N-70-5 sample after equilibrium swelling in water, solvent exchange, and drying, FIG. 4C shows the microstructure of a dry N-85-5 sample before it has been exposed to water, and FIG. 4D shows the microstructure of a dry N-85-5 sample after equilibrium swelling in water, solvent exchange, and drying;

FIGS. 5A-B present the results of the compressive stress-strain studies conducted using fully swollen compositions-of-matter and corresponding reference bulk hydrogels, wherein FIG. 5A presents the results on a compressive stress scale of 0-0.062 MPa and FIG. 5B presents the results on a compressive stress scale of 0-0.27 MPa;

DESCRIPTION OF SPECIFIC EMBODIMENTS OF THE INVENTION

Figure 1:
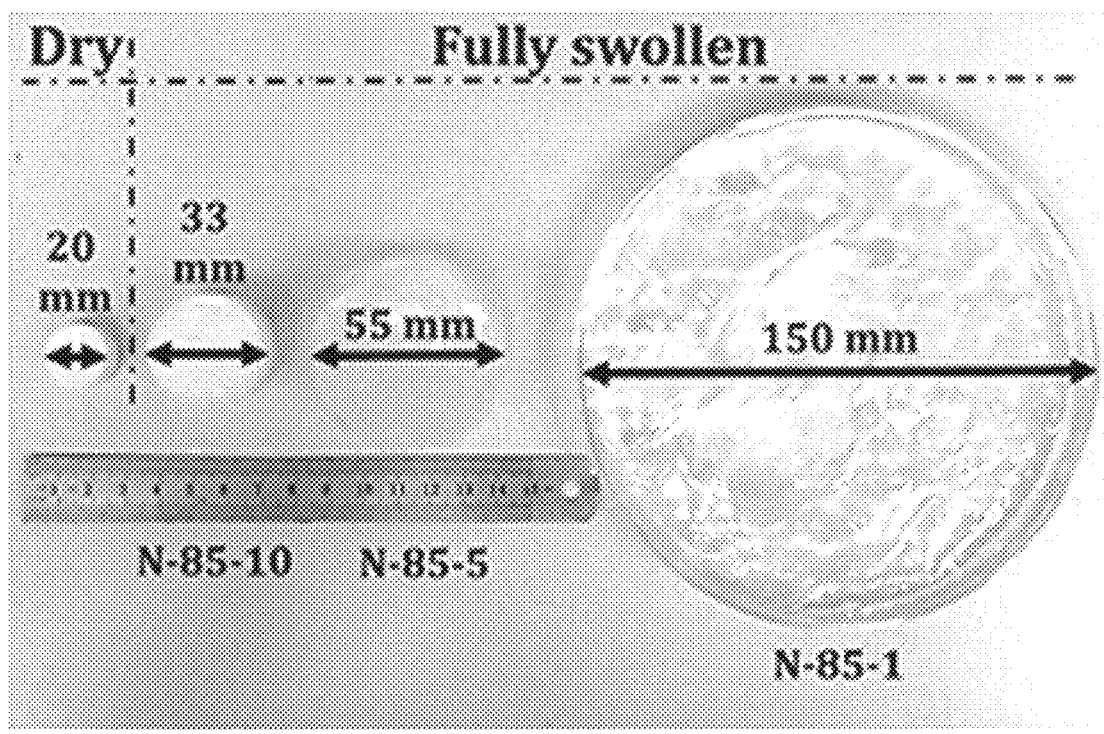
FIG. 1 presents a photograph of an exemplary composition-of-matter, according to some embodiments of the present invention, N-85-y, showing the extensive change in dimensions of the sample upon equilibrium swelling, as a function of various degrees of crosslinking (y=10, 5 and 1, left to right)

The present invention, in some embodiments thereof, relates to material science, and more particularly, but not exclusively, to superabsorbent polymeric hydrogels and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, superabsorbent polymers have a wide range of uses and applications, however these are limited by the low compressive strain attainable by these polymers, which tend to fail easily in both dry and swollen (wet) forms. While searching for a comprehensive solution to the problem of brittleness of superabsorbent polymers, the present inventors have contemplated a polymer substantially comprising ionic/ionizable pendant groups (side-chain moieties), which can exhibit both superabsorbency and mechanical durability. The inventors have further contemplated using a HIPE as a structural template for the polymer; however, as known in the art, ionic monomers which are polymerized from aqueous media will render the corresponding oil-in-water HIPE difficult to stabilize through the polymerization step.

While reducing the invention to practice, and while considering the difficulties regarding oil-in-water HIPE stabilization in general and ionic monomer HIPEs in particular, the present inventors have surprisingly succeeded to form a polyHIPE made primarily from ionic/ionizable monomers, which had both desired properties, superabsorbency and mechanical durability when fully swollen with an aqueous medium. The newly formed superabsorbent polyHIPE compositions-of-matter exhibited extraordinary water (up to about 1000 gram per gram) and artificial urine absorptions (up to 90 gram per gram), as well as the ability to reach 60% compressive strain without failing while retaining the absorbed liquid. The newly formed superabsorbent polyHIPE composition-of-matter presented herein also exhibited ion exchange capacities and water-soluble dye removal capacities.

Studies of the mechanism of action of the presently provided composition-of-matter lead to the understanding that the polyHIPE microstructure allows hydrogel-swelling-driven void expansion that can produce almost a four-fold increase in void size (see, e.g., sample N-85-5 in the Examples section below). In the swollen state, the highly accessible ionic pendant groups of the polymer can produce an ion exchange capacity of about 7 meq NaOH per gram polymer and dye absorption of at least 3.1 mmol per gram polymer.

The swollen compositions-of-matter does not fail like commercially known superabsorbent polymers, even at compressive strains of about 60%, and they recover their shape upon removal of the stress; and they are even tougher in the dry form.

It was further discovered that augmentation in the crosslinking level of the polyHIPE can greatly influence superabsorbency and mechanical durability. In addition it was found that the synthesis of a polyHIPE can enhance the water uptake and, by affecting the deformation mechanism, can also enhance the toughness. It was surprising that synthesis of a polyHIPE affected the deformation mechanism and produced a significant increase in the maximum strain attainable without failure, hydrated or dry.

These superabsorbent polyHIPE compositions-of-matter, with their extraordinary combination of absorption capacities and mechanical properties, can be used as effective adsorbents for a plethora of applications including wastewater remediation and personal hygiene products.

Superabsorbent Polymeric Compositions-of-Matter:

Thus, according to an aspect of some embodiments of the present invention, there is provided a superabsorbent polymeric composition-of-matter having a microstructure of a polymerized external phase of a high internal phase emulsion (HIPE).

The superabsorbent polymeric compositions-of-matter presented herein are HIPE-templated, namely their microstructure is a projection of the microstructure of a HIPE before and after its polymerization. Briefly, a HIPE is a plurality of tightly-packed spheroidal droplets of various sizes, constituting the dispersed phase, separated by walls of a liquid constituting the continuous phase. The average size and size distribution of the droplets is controlled by the chemical composition and mechanical treatment of the emulsion phases, and are typically characterized by a population of narrowly distributed sizes. For example, size droplet size average and distribution can be controlled by use of emulsion stabilizers (surfactants; surface-active substances etc.), which may act to reduce the tendency of the droplets to coalesce. The resulting reduction in coalescence yields relatively narrow droplet size distributions that can be used to produce polyHIPEs with narrowly distributed void size.

The term "polyHIPE" can therefore be used as a structural term to describe a highly porous monolithic structure of thin walls separating a collection of tightly-packed spheroidal voids. The walls are thinner at the closest distance between what was tightly-packed droplets before polymerization, and thicker at the spaces between adjacent droplets. When a HIPE is polymerized to yield a polyHIPE, the same microstructure is substantially preserved, while at their thinnest areas some of the walls give way to interconnecting windows connecting adjacent spheroidal droplets.

When the polyHIPE is dried off and the dispersed phase is removed, the droplets leave spheroidal voids in their place, which are interconnected by the windows in the walls, making the microstructure an open-cell microstructure, wherein the voids are referred to as cells. Hence the term "HIPE-templated" is a structural term rather than a process-related term, since it relates the microstructure of the HIPE (or polyHIPE) to the microstructure of the resulting monolithic polymeric composition-of-matter, which is no longer an emulsion but a solid matter.

According to some embodiments of the present invention, the microstructure of the superabsorbent polymeric compositions-of-matter is structurally-templated by an oil-in-water high internal phase emulsion, or HIPE. In an oil-in-water HIPE the polymerization reaction takes place essentially in the aqueous continuous external phase, while the organic dispersed internal phase serves at the pore-forming factor, making spherical voids in the continuous external phase.

In the context of embodiments of the present invention, the phrase "superabsorbent HIPE-templated monolithic polymeric composition-of-matter", is used herein to refer to the presently provided and claimed macroscopic entities, which are characterized by superabsorbency of aqueous media, by having an open-cell porous microstructure projected by its structural precursor being a high internal phase emulsion (HIPE), by its consistency being a monolithic and highly porous polymeric structure, and by having unique mechanical properties that are derived from its structural, mechanical and chemical composition. The phrase "superabsorbent HIPE-templated monolithic polymeric composition-of-matter" is used herein interchangeably with the phrases "polymeric composition-of-matter", "superabsorbent monolithic composition-of-matter", "superabsorbent polymeric composition-of-matter", "superabsorbent HIPE-templated composition-of-matter", "superabsorbent porous composition-of-matter", "HIPE-templated composition-of-matter", "superabsorbent composition-of-matter" or "composition-of-matter".

Density:

The composition-of-matter presented herein is porous mainly due to the polyHIPE microstructure (voids) and also due to the porosity of the bulk polymer; according to some embodiments of the present invention, the composition-of-matter is characterized by a dry density that ranges from 0.05 $g/cm^3$ to 0.4 $g/cm^3$, namely that when the composition-of-matter is completely dry (dried under vacuum until its mass stays constant), between 95% to 60% of its volume is empty (filled with air). In some embodiments, the dry density of the composition-of-matter is about 0.5 $g/cm^3$, 0.48 $g/cm^3$, 0.46 $g/cm^3$, 0.44 $g/cm^3$, 0.42 $g/cm^3$, 0.4 $g/cm^3$, 0.38 $g/cm^3$, 0.36 $g/cm^3$, 0.34 $g/cm^3$, 0.32 $g/cm^3$, 0.3 $g/cm^3$, 0.28 $g/cm^3$, 0.26 $g/cm^3$, 0.24 $g/cm^3$, 0.22 $g/cm^3$, 0.2 $g/cm^3$, 0.18 $g/cm^3$, 0.16 $g/cm^3$, 0.14 $g/cm^3$, 0.12 $g/cm^3$, 0.1 $g/cm^3$, 0.08 $g/cm^3$, 0.06 $g/cm^3$ or 0.04 $g/cm^3$.

In some embodiments of the present invention, the voids or pores in the microstructure of the composition-of-matter presented herein, are interconnected in what is known as an open-cell configuration. In an open-cell configuration the walls separating the voids have "windows", and so the entire space not occupied by the polymer is accessible to water and other solvents and solutes. Without being bound by any particular theory, it is assumed that the presence of windows (open-cell microstructure) allows for the great contribution of hydrogel-swelling-driven void expansion, discussed hereinbelow.

Crosslinking Level:

In some embodiments of the present invention, the polymerized external phase is a crosslinked polymer. Typically, the more crosslinked a polymer, the more compressible it is (can be compressed without failing), up to a crosslinking level where it becomes rigid. This trait is also observed in polymeric hydrogels.

A crosslink is a bridge between polymeric chains, which is made by placing "crosslinking units" between "regular main-chain units" or "main-chain positions"; the more crosslinking units being incorporated in the main-chain positions, the higher is the crosslinking level. According to some embodiments, the polymer constituting the composition-of-matter is crosslinked to a level that ranges from a high of 15 crosslinking units per 100 main-chain positions (including monomeric unit positions and crosslinking unit positions), to a low of 0.1 crosslinking units per 100 main-chain positions. In some embodiments, the crosslinking level ranges from 0.1 to 10, from 1 to 15, or from 1 to 10 crosslinking units per 100 main-chain positions. In some embodiments, the crosslinking level is about 15, 14, 13, 12, 11, 10, 9, 8, 7, 6, 5, 4, 3, 2, 1, 0.5 or about 0.1 crosslinking units per 100 main-chain positions. One crosslinking unit per one hundred main-chain positions is equivalent to a crosslinking level of one molar (mol) percent.

As demonstrated in the Examples section below, the crosslinking level is one of the factors that govern the mechanical properties of the composition-of-matter presented herein, as well as its aqueous medium absorption capacity, whereas the two traits react inversely to the crosslinking level; absorption decreases with the increase of the crosslinking level while stiffness and deformability increase with the increase of the crosslinking level.

Ionizable Pendant Groups:

According to some embodiments of the present invention, the polymer is characterized also by its pendant groups, wherein at least a portion thereof are ionic or ionizable pendant groups. According to some embodiments of the present invention, the ratio of ionizable pendant groups to non-ionizable pendant groups in the crosslinked polymer of the composition-of-matter presented herein is greater than 85 percent. In some embodiments, the ratio of ionizable pendant groups to non-ionizable pendant groups in the crosslinked polymer is about or greater than about 85%, 86%, 87%, 88%, 89%, 90%, 91%, 92%, 93%, 94%, 95%, 96%, 97%, 98% or 99%. According to some embodiments of the present invention, the polymer essentially has only ionizable pendant groups (not accounting for crosslinks), and is essentially devoid of non-ionizable pendant groups.

In the context of embodiments of the present invention, the terms "ionic" and "ionizable" are used interchangeably to describe the electrostatic character of a chemical entity such as a molecule, a moiety/group, a monomer, a pedant group of a polymer or an entire polymer. In the context of embodiments of the present invention, an ionic or ionizable entity is one that exhibits a charged at, or near, neutral pH (pH 5-9 or 6-8) in an aqueous medium.

Ionizable functional or pendant groups include negatively-charged groups and positively-charged groups.

According to some embodiments the ionizable pendant groups consists of negatively-charged groups. Alternatively, according to some embodiments, the ionizable pendant groups consists of positively-charged groups. Exemplary positively-charged groups include, without limitation, amino (amine) groups that can be protonated to form an ammonium group. Exemplary negatively-charged groups include, without limitation, carboxylic (acetic) group, sulfo group, sulfino group, phosphate group and phosphono group.

As used herein, the terms "carboxylic group", "acetate group" or "acetic group" refer to an $RCO_2H$ group, wherein R represents the polymer.

As used herein, the terms "sulfo group" or "sulfonic group" refer to an organosulfur $RSO_3H$ group, wherein R represents the polymer.

As used herein, the terms "sulfino group" or "sulfinic group" refer to an organosulfur $RSO_2H$ group, wherein R represents the polymer.

The term "sulfate group" refers to an organosulfur $ROSO_3H$ group, wherein R represents the polymer.

The term "phosphono group" or "phosphonic acid group", as used herein, refers to an organophosphorous $RP(=O)(OH)_2$ group, wherein R represents the polymer.

As used herein, the term "phosphate group" refers to an organophosphorous $ROP(=O)(OH)_2$ group or an $ROP(=O)(OH)_2$ group, wherein R represents the polymer.

Level of Hydration of Ionizable Pendant Groups:

Despite the well-known inherent difficulty in stabilizing a HIPE having ionizable monomers en route to producing a polyHIPE with ionizable pendant groups, the present inventors have attempted to make such a polyHIPE with even more "ionic" pendant groups that were previously reported in the art, e.g., poly(acrylic acid) polyHIPE. In the context of the present invention, "more ionic" refers to the propensity of the pendant groups to bind water molecules, or in other words, a greater propensity to be hydrated. Thus, according to embodiments of the present invention, the ionizable pendant groups of the polymer are selected according to their level of hydration (solvation by water) on the Hofmeister Series scale so as to be more strongly hydrated than an carboxylic (acetic/acetate) pendant group.

As known in the art, the Hofmeister Series scale ranks ions and ionizable groups according to their ability to salt out or salt in proteins; following the same rationale, in the context of the present invention, the ionizable pendant groups are seen as charged ions interacting with water. According to the Hofmeister Series scale, acetate, such as the pendant group in a poly(acrylic acid), is less strongly hydrated than a phosphate, sulfate or sulfonate pendant group.

According to some embodiments of the present invention, the ionizable pendant groups of the crosslinked polymer of the presently composition-of-matter, belong to the organosulfur group family. In some embodiments, the organosulfur group is one of sulfonate and sulfate, or a blend thereof. In some embodiments, the organosulfur group is a sulfonate. According to some embodiments of the present invention, the crosslinked polymer comprises poly(2-acrylamido-2-methylpropanesulfonic acid), which is a polymer characterized by 2-((carbonyl)amino)-2-methylpropane-1-sulfonic acid pendant groups.

The combination of microstructure, being a highly-porous polyHIPE, and chemical composition, being a crosslinked ionizable polymer with highly hydratable pendant groups, the composition-of-matter presented herein is characterized by high aqueous absorbency and exceptionally high mechanical durability, even when fully hydrated.

Aqueous Media Absorption:

The composition-of-matter presented herein is capable of absorbing aqueous media far more than a comparable substance made from the same polymer. In the Examples section that follows, such comparable substance is referred to as a reference bulk hydrogel or a reference bulk polymer. Without being bound by any particular theory, it is assumed that the ability to swell and absorb water, which is common to both the composition-of-matter and the corresponding reference bulk polymer, is overshadowed many folds by hydrogel-swelling-driven void expansion that produces a multi-fold increase in void size. If the composition-of-matter was acting only as a sponge, the voids would be filled with the medium, however, the unique combination of structure and composition allows the composition-of-matter presented herein to absorb aqueous medium at a rate of at least 8 g/g at equilibrium.

In some embodiments the equilibrium absorption of aqueous medium exhibited by the composition-of-matter presented herein is at least 10 g/g, 12 g/g, 14 g/g, 16 g/g, 18 g/g, 20 g/g, 25 g/g, 30 g/g, 35 g/g, 40 g/g, 45 g/g, 50 g/g, 60 g/g, 70 g/g, 80 g/g, 90 g/g, 100 g/g, 150 g/g, 200 g/g, 250 g/g, 300 g/g, 350 g/g, 400 g/g, 450 g/g, 500 g/g, 600 g/g, 700 g/g, 800 g/g, 900 g/g or at least 1000 grams aqueous medium per one gram of the composition-of-matter.

For example, according to an embodiments of the present invention, a composition-of-matter comprising 85% polymer (internal phase content) and 0.1% level of crosslinking agent (coded N-85-0.1) has been shown to absorb up to about 800 g/g, and a composition-of-matter comprising 70% polymer (internal phase content) and 0.1% level of crosslinking agent (coded N-70-0.1) has been shown to absorb up to about 1000 g/g.

Mechanical Properties:

As stated hereinabove, while many superabsorbent polymers can show a high level of water absorption, none can show the same while being mechanically durable, such as in sustaining considerable compressive strain. All known superabsorbent polymers fail under mild compressive strain, and most irreversibly lose their liquid contents when compressed.

In the context of embodiments of the present invention, the terms "failure" and "failing" is a mechanical term defined as a non-negligible decrease in stress with increasing strain or a discontinuity in the stress with increasing strain. In some cases, a discontinuity in the stress with increasing strain may be noticeable in a stress/strain plot as a sharp change in the trend of an otherwise smooth curve. A material could "fail" but such a failure might not be visually obvious or otherwise seen as macroscopic structural damage. In some cases, failure may be expressed visibly as breakage or cracks. It is noted that materials may undergo an irreversible deformation (plastic deformation) without failing. For example, dry samples of the composition—of matter, according to some embodiments of the present invention, did not recover their shape entirely or perfectly after reaching 70% strain, yet they did not "fail" in the sense that the stress continued to increase with increasing strain (no discontinuity was observed in the stress/strain plot).

Unprecedentedly, the composition-of-matter presented herein is capable of sustaining a compressive strain ($\sigma_{F-SW}$) of at least 25% before failing (compressive failure strain in percent), when the composition-of-matter is fully swollen with aqueous medium.

In some embodiments the composition-of-matter presented herein will not lose the absorbed medium upon compression, or will re-absorb the liquid when the stress is removed.

In some embodiments, the composition-of-matter is characterized by a compressive failure strain when fully swollen ($\sigma_{F-SW}$) of at least 26%, 28%, 30%, 32%, 34%, 36%, 38%, 40%, 42%, 44%, 46%, 48%, 50%, 52%, 54%, 56%, 58%, 60%, 62%, 64%, 66%, 68% or at least 70% when the composition-of-matter is fully swollen by an aqueous medium.

In some embodiments, the composition-of-matter is characterized by a compressive failure strain when fully swollen ($\sigma_{B-SW}$), which is at least 2-fold, 4-fold, 6-fold, 8-fold, or more than 10-fold greater than the compressive failure strain observed in the corresponding reference bulk hydrogel, which is made of the same crosslinked polymer but not in a polyHIPE configuration. This comparison will hold for two samples of equal or similar shape and size.

The composition-of-matter presented herein can be further characterized by various other mechanical properties, such as the modulus of fully swollen at equilibrium ($E_{SW}$); the modulus of the dry composition-of-matter ($E_D$), the stress at fail in the swollen state ($\sigma_{B-SW}$), and the stress at 70% compressive strain in the dry state ($\sigma_{70-D}$).

In some embodiments, the modulus of a fully swollen composition-of-matter is at least 4 kPa, 5 kPa, 6 kPa, 7 kPa, 8 kPa, 9 kPa, 10 kPa, 11 kPa, 12 kPa, 13 kPa, 14 kPa, 15 kPa, 16 kPa, 17 kPa, 18 kPa, 19 kPa, 20 kPa, 25 kPa, 30 kPa, 35 kPa, 40 kPa, 45 kPa, 50 kPa, 55 kPa or at least 60 kPa.

In some embodiments, the modulus of a dry composition-of-matter is at least 300 kPa, 350 kPa, 400 kPa, 450 kPa, 500 kPa, 550 kPa, 600 kPa, 650 kPa, 700 kPa, 750 kPa, 800 kPa, 850 kPa, 900 kPa, 950 kPa, 1000 kPa, 1100 kPa, 1200 kPa, 1300 kPa, 1400 kPa, 1500 kPa, 1600 kPa, 1700 kPa, 1800 kPa, 1900 kPa, 2000 kPa, 2500 kPa, 3000 kPa, 3500 kPa, 4000 kPa, 4500 kPa, 5000 kPa, 10000 kPa, 20000 kPa, 30000 kPa, 40000 kPa, 50000 kPa, 60000 kPa, 70000 kPa, 80000 kPa, 90000 kPa or at least 100000 kPa.

In some embodiments, the stress at fail in the fully swollen state is at least 4 kPa, 5 kPa, 6 kPa, 7 kPa, 8 kPa, 9 kPa, 10 kPa, 11 kPa, 12 kPa, 13 kPa, 14 kPa, 15 kPa, 16 kPa, 17 kPa, 18 kPa, 19 kPa, 20 kPa, 25 kPa, 30 kPa, 35 kPa, 40 kPa, 45 kPa, 50 kPa, 55 kPa or at least 60 kPa.

In some embodiments, the stress at fail at 70% compressive strain when dry is at least 300 kPa, 350 kPa, 400 kPa, 450 kPa, 500 kPa, 550 kPa, 600 kPa, 650 kPa, 700 kPa, 750 kPa, 800 kPa, 850 kPa, 900 kPa, 950 kPa, 1000 kPa, 1100 kPa, 1200 kPa, 1300 kPa, 1400 kPa, 1500 kPa, 1600 kPa, 1700 kPa, 1800 kPa, 1900 kPa, 2000 kPa, 2500 kPa, 3000 kPa, 3500 kPa, 4000 kPa, 4500 kPa, 5000 kPa, 10000 kPa, 20000 kPa, 30000 kPa, 40000 kPa, 50000 kPa, 60000 kPa, 70000 kPa, 80000 kPa, 90000 kPa or at least 100000 kPa.

HIPE Composition:

The density of the composition-of-matter presented herein also depends on the ratio of internal to external phase in the precursor HIPE. The more internal phase, the less dense the resulting composition-of-matter is; the internal phase is removed once the external phase is polymerized, leaving behind empty voids. According to some embodiments of the present invention, the mass ratio of the external phase to internal phase is about 50% (50 parts internal phase to 100 parts HIPE), 48%, 46%, 44%, 42%, 4%, 38%, 36%, 34%, 32%, 30%, 28%, 26%, 24%, 22%, 20%, 18%, 16%, 14%, 12%, 10%, 8%, 6% or 4% of the total HIPE mass.

When referring to the chemical composition of a polymer, such as the one comprising the presently provided composition-of-matter, one may refer to the chemical composition of the external phase of the HIPE, or the pre-polymerization mixture that preceded polyHIPE, namely the mixture of monomers, crosslinking agents, initiators and other ingredients which were present and contributed to the polymerization step; the contents of the pre-polymerization mixture therefore defines the chemical composition of the polymer that is formed therefrom, at least to the extent of the chemical composition of the backbone (main chain) and pendant groups (side chain residues). According to some embodiments of the present invention, the HIPE is an oil-in-water HIPE, meaning that the external phase is an aqueous pre-polymerization mixture. In the case of the presently provided the composition-of-matter, the pre-polymerization mixture comprises at least one type of monomer and at least one type of crosslinking agent, while other ingredients may include an initiator, an accelerating agent (typically a reducing agent), and other factors that affect the polymerization process, or do not.

In some embodiments, the HIPE includes self-crosslinking monomers, such as, but not limited to N,N-dimethylacrylamide (DMAA).

In some embodiments, the internal phase is an organic hydrophobic, water-immiscible solvent or a mixture of more than one such solvent. Examples of water-immiscible solvents include, without limitation, toluene, xylene, tichloroethylene, any hydrocarbon-based oil, and silicone-based oil, di-iso-propyl ether, pentane, methyl-ethyl ketone, methyl-t-butyl ether, hexane, heptane, di-ethyl ether, ethyl acetate, dichloromethane, 1,2-dichloroethane, cyclohexane, chloroform, carbon tetrachloride, butyl acetate, n-butanol, benzene, and any combination thereof.

Surfactants:

The HIPE is stabilized by a surfactant. According to some embodiments of the present invention, the surfactant is a hydrophilic non-ionic surfactant. Exemplary hydrophilic non-ionic surfactants include, without limitation, poloxamers, members of the alkylphenol hydroxypolyethylene family and a polyethoxylated sorbitan esters (polysorbitans).

In some embodiments, the surfactant is Poloxamer 407, Triton X-405, Triton X-100, Triton X-705 and Tween 20.

Ionizable Monomers:

According to some embodiments, the pre-polymerization mixture includes ionic/ionizable monomers that constitute at least 85 percent of the monomers (not accounting for the crosslinking agent) in the pre-polymerization mixture. This high content of ionic monomers is notable since, as known in the art, stabilization of an oil-in-water HIPE having a majority of ionic monomers in the external phase is oftentimes impossible to maintain through the polymerization process. In some embodiments, the ratio of ionizable monomers to non-ionizable monomers in the pre-polymerization mixture is about or greater than about 85%, 86%, 87%, 88%, 89%, 90%, 91%, 92%, 93%, 94%, 95%, 96%, 97%, 98% or 99%, based on the total amount of the pre-polymerization mixture. According to some embodiments of the present invention, the pre-polymerization consists essentially of ionizable monomers and crosslinking agents, and is essentially devoid of non-ionizable monomers.

The pre-polymerization mixture may comprise any type of ionizable monomers. In some embodiments, the ionizable monomers exhibit a non-polymerizing functional group (a group that corresponds to the pendant group on the resulting polymer) such as, without limitation, carboxylic (acetic) group, sulfo group, sulfino group, phosphate group and phosphono group. In some embodiments, the ionizable monomers are selected from the family of sulfur-containing monomers (the organosulfur family), the phosphorous-containing monomers (the organophosphorous family) and any combination thereof.

Exemplary ionizable monomers of the organosulfur family include, without limitation, 2-acrylamido-2-methylpropane sulfonic acid (AMPS), 2-acrylamido-2-propanesulfonic acid, 1-acrylamido-1-propanesulfonic acid, 2-(methacryloyloxy)ethanesulfonic acid, 2-hydroxy-3-(2-propenyloxy)-propanesulfonic acid, 2-methacrylamido-2-methyl-1-propanesulfonic acid, 2-methyl-2-propene-1-sulfonic acid, 2-propene-1-sulfonic acid, 2-sulfoethyl acrylate, 2-sulfoethyl methacrylate, 3-methacrylamido-2-hydroxypropanesulfonic acid, 3-sulfopropyl acrylate, 3-sulfopropyl methacrylate, 3-sulfopropylacrylate, 3-sulfopropylmethacrylate, allyl sulfonic acid, allyloxybenzenesulfonic acid, methallyloxybenzenesulfonic acid, methallylsulfonic acid, phenylethenesulfonic acid, styrenesulfonic acid, sulfomethacrylamide, sulfomethylmethacrylamide, vinylsulfonic acid, and any salts thereof, and any combinations thereof.

Exemplary ionizable monomers of the organophosphorous family include, without limitation, 2-methacrylamidoethylphosphoric acid, isopropenylphosphonic acid, methacrylamide phosphonic acid, isopropenylphosphonic acid, vinylphosphonic acid, isopropenylphosphonic anhydride, allylphosphonic acid, ethylidenediphosphonic acid, vinylbenzenephosphonic acid, 3-allyloxy-2-hydroxypropylphosphonic acid, and any salts thereof, and any combinations thereof.

In some embodiments, the HIPE includes comonomers, such as, but not limited to hydroxyethyl methacrylate, hydroxyethyl acrylate, acrylamide, acrylic acid, methacrylic acid, 1-vinylimidizole, styrene sulfonate and combinations thereof. According to some embodiments, the comonomers constitute less than 10% of the polymerizable phase (continuous, aqueous phase), or less than 5%, or less than 1% of the polymerizable phase. According to some embodiments, the comonomers constitute about 0.5, 1, 5, 10 or 20% of the polymerizable phase.

Crosslinking Agents:

The crosslinking level is determined by the amount of the crosslinking agent in the pre-polymerization mixture, relative to the number of monomers therein.

Hence, the crosslinking level is defined by mol percent of the crosslinking agent in the total polymerizable units that constitute the polymer. According to some embodiments, the amount of the crosslinking agents in the pre-polymerization mixture ranges from a high of 15 mol percent to a low of about 0.5 mol percent, based on the total number of moles of polymerizable units (monomers and crosslinking agents), that constitute the pre-polymerization mixture.

In some embodiments, the crosslinking level of the polymer in the composition-of-matter is about 15 mol %, 14.5 mol %, 14 mol %, 13.5 mol %, 13 mol %, 12.5 mol %, 12 mol %, 11.5 mol %, 11 mol %, 10.5 mol %, 10 mol %, 9.5 mol %, 9 mol %, 8.5 mol %, 8 mol %, 7.5 mol %, 7 mol %, 6.5 mol %, 6 mol %, 5.5 mol %, 5 mol %, 4.5 mol %, 4 mol %, 3.5 mol %, 3 mol %, 2.5 mol %, 2 mol %, 1.5 mol %, 1 mol %, or 0.5 mol %.

The type of crosslinking agent is selected according to its compatibility with the other polymerizable units and the conditions of the polymerization reaction. The crosslinking agent is also selected according to its solubility, wherein a crosslinking agent that can dissolve in the pre-polymerizable mixture together with the monomers will be a natural choice, while crosslinking agents that can dissolve in the other phase but can cross the phase boundary during the polymerization process are also contemplated. For example, ethylene glycol dimethacrylate (EGDMA) is hydrophobic and can dissolve more readily in the internal organic phase, and it is contemplated as a crosslinking agent since it has been shown to take part in a polymerization reaction of an emulsion that occurs in the aqueous phase.

Non-limiting examples of crosslinking agents include N,N'-methylenebisacrylamide (MBAAm) ethylene glycol diacrylate, diethylene glycol diacrylate, N-(1-hydroxy-2,2-dimethoxyethyl)acrylamide, N,N'-(1,2-dihydroxyethylene) bisacrylamide, and any combination thereof.

Applications and Uses:

The composition-of-matter presented herein is designed to absorb and contain, in the form of a hydrogel, any type of an aqueous solution, even under considerable compressive strain. The ionic nature of the pendant groups allows deionized water as well as water containing any solutes (salts and other water-soluble chemical entities) to be absorbed in the composition-of-matter. As demonstrated in the Examples section below, the composition-of-matter presented herein, according to some embodiments of the present invention, were shown to be highly effective in absorbing water and urine at considerable mass ratios, while maintaining a notable resistivity to compressive strain, substantially without losing the absorbed liquid.

Thus, the composition-of-matter can serve as excellent liquid absorption and/or retention hydrogel substance and matrix for a variety of uses.

According to an aspect of some embodiments of the present invention, the composition-of-matter form a part or be an article of manufacturing, either in the dry or the wet form as partially hydrated, partially swollen or fully swollen hydrogels.

Due to their unique mechanical properties, the composition-of-matter can be cast in the liquid HIPE form into any shape and size mold before polymerization, or they can be reshaped and further processed post casting and polymerization in the dry or wet form. The composition-of-matter can therefore take any size of a block, a sphere, a rod, a particle (powder), a flat or shaped sheet, a tube or a fiber.

The article of manufacturing in which the composition-of-matter is incorporated can be any one of the non-limiting examples that include a diaper, an incontinence garment, a fire-retardant material or device, a flood/spill control material or device, a fragrance carrier, thermal pack, a liquid waste material or device, an ion-exchange material or device, a filter material or device, a water purification material or device, a surgical pad, a water retention material or container device, a cosmetic product, a personal hygiene product, a personal care product, a grooming product and a wound dressing.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Materials and Methods

In some embodiments, the monolithic superabsorbent HIPE-templated hydrogel structure (composition-of-matter) presented herein is based on poly(2-acrylamido-2-methylpropanesulfonic acid) (PAMPS), crosslinked with N,N'-methylenebisacrylamide (MBAAm), templating oil-in-water HIPE.

Materials:

Ionic monomer: 2-acrylamido-2-methylpropanesulfonic acid (AMPS; Sigma-Aldrich); crosslinking agent: methylene bisacrylamide (MBAAm; Sigma-Aldrich); surfactant: commercial triblock copolymer based poly(ethylene glycol) (PEG) and poly(propylene glycol) (PPO) (Poloxamer 407 hydrophilic non-ionic surfactant; Pluronic™ F127, a PEG-b-PPO-b-PEG with 70% PEG having Mw=12,600 g/mol and 70% PEG; Sigma-Aldrich); initiator: ammonium persulfate (APS; Fluka); reducing agent: N,N,N',N'-tetramethylethylenediamine (TEMED; Sigma-Aldrich); solvents: toluene (Sigma-Aldrich), ethanol (Sigma-Aldrich), ether (Sigma-Aldrich); visible indicator: methylene blue (MB; Sigma-Aldrich). Other materials were used as-is from various sources.

Methods:

A critical principle in the preparation of the composition-of-matter presented herein, is to generate an oil-in-water HIPE with sufficient kinetic stability that remains stable during polymerization of the HIPE. While a typical oil-in-water HIPE requires relatively high concentrations of surfactant serving as a stabilizing emulsifier (between 20-30 percent by weight of the continuous phase), and oftentimes requires a combination of surfactants, the presently provided oil-in-water HIPE of an ionic/ionizable monomer surprisingly required only 3-5% surfactant (by weight of the continuous phase) for sufficient stability.

AMPS, MBAAm, APS, deionized H$_2$O and Pluronic F127 were placed in a 100 mL beaker and the mixture was stirred with an overhead stirrer at 400 rpm. Thereafter, a corresponding amount of toluene was added drop-wise under constant stirring. Once all toluene had been added, stirring was continued for a further 10 minutes, to enhance the uniformity of the oil-in-water HIPE. The resulting highly stable HIPEs did not undergo phase separation even after 48 hours at 50° C., and remained stable for over 1 hour at 80° C.

After stirring at reduced rate of 20 rpm, the reducing agent TEMED was added followed by additional 3 minutes of stirring at 20 rpm, and the emulsion was transferred to a glass vial and cured for 24 hours at 40° C. The resulting polyHIPEs were washed using Soxhlet extraction with ethanol and ether, each for 24 hours, and dried under vacuum until a constant weight was obtained.

Tables 1A and Table 1B below presents some exemplary HIPE recipes, according to some embodiments of the present invention, wherein sample codes follow the format "N-x-y", with x representing the internal phase content by approximation (70 or 85 percent internal phase by weight of the total weight of the HIPE), and y representing the level of crosslinking in content of crosslinking agent with respect to the total amount monomer(s) by approximation (0.1, 0.5, 1, 5, or 10 percent crosslinker by weight of the total amount of polymerizable units).

TABLE 1A

| Sample code: | N-70-0.1 | N-70-0.5 | N-70-1 | N-70-5 | N-70-10 |
|---|---|---|---|---|---|
| Aqueous External Phase, weight % | | | | | |
| H$_2$O (Solvent) | 19.783 | 19.777 | 19.75 | 19.71 | 19.58 |
| AMPS (ionic monomer) | 9.931 | 9.928 | 9.92 | 9.89 | 9.83 |

TABLE 1A-continued

| Sample code: | N-70-0.1 | N-70-0.5 | N-70-1 | N-70-5 | N-70-10 |
|---|---|---|---|---|---|
| MBAAm (crosslinker) | 0.011 | 0.037 | 0.11 | 0.39 | 1.05 |
| F127 (surfactant) | 1.583 | 1.582 | 1.58 | 1.58 | 1.57 |
| APS (initiator) | 0.396 | 0.396 | 0.40 | 0.39 | 0.39 |
| TEMED (reducer) | 0.246 | 0.246 | 0.25 | 0.24 | 0.24 |
| Total | 31.948 | 31.966 | 32.01 | 32.20 | 32.66 |
| Organic Internal Phase, weight % | | | | | |
| Toluene | 68.050 | 68.034 | 67.99 | 67.80 | 67.34 |
| Total | 68.052 | 68.034 | 67.99 | 67.80 | 67.34 |

TABLE 1B

| Sample code: | N-85-0.1 | N-85-0.5 | N-85-1 | N-85-5 | N-85-10 |
|---|---|---|---|---|---|
| Aqueous External Phase, weight % | | | | | |
| H$_2$O (Solvent) | 8.379 | 8.378 | 8.38 | 8.34 | 8.34 |
| AMPS (ionic monomer) | 4.206 | 4.206 | 4.20 | 4.20 | 4.19 |
| MBAAm (crosslinker) | 0.005 | 0.016 | 0.04 | 0.17 | 0.45 |
| F127 (surfactant) | 0.67 | 0.67 | 0.67 | 0.67 | 0.67 |
| APS (initiator) | 0.168 | 0.168 | 0.17 | 0.17 | 0.17 |
| TEMED (reducer) | 0.104 | 0.104 | 0.10 | 0.10 | 0.10 |
| Total | 13.532 | 13.541 | 13.56 | 13.65 | 13.92 |
| Organic Internal Phase, weight % | | | | | |
| Toluene | 86.468 | 86.458 | 86.44 | 86.35 | 86.08 |
| Total | 86.468 | 86.459 | 86.44 | 86.35 | 86.08 |

The level of crosslinking can also be defined as the number of crosslinking agent molecules as a percent of total number of polymerizable units, namely a molar percent. In the exemplary samples presented in Table 5, the crosslinking level in terms of molar percentage (mol %) of MBAAm, was 0.14 in N-70-0.1, 0.50 in N-70-0.5, 1.47 in N-70-1, 5.03 in N-70-5, 12.56 in N-70-10, 0.16 in N-85-0.1, 0.50 in N-85-0.5, 1.26 in N-85-1, 5.16 in N-85-5 and 12.62 in N-85-10.

Elemental analysis indicated that N-70-10 and N-85-10 contained 10.1 and 9.9 weight percent sulfur, respectively, corresponding to 3.1 mmol of sulfonic acid groups per gram of polymer.

Reference bulk hydrogels (non-polyHIPE hydrogels) were synthesized using the same ratios of water, monomers, initiator, and reducing agent as the recipes in Table 1, but without the surfactant and the organic phase. Reference hydrogels sample codes follow the format "R-y", wherein y indicates the MBAAm content in the total monomers.

Before drying, all specimens were purified by Soxhlet extraction with ethanol and ether to remove all non-polymerized species.

Density:

The HG-PH and HG-R densities ($\rho_{PH}$ and $\rho_{HG}$, respectively) were determined gravimetrically. The HG-PH skeletal (polymer wall) densities ($\rho_P$) were evaluated using a fully automated, high-precision helium pycnometer (Micromeritics AccuPyc II 1340). The samples were thoroughly dried and purged to exclude moisture and adsorbed impurities prior to the measurement (average of ten consecutive measurements).

Scanning Electron Microscopy (SEM):

Morphology, porosity and microstructure studies of cryogenic fracture surfaces of dry samples of the composition-of-matter, according to some embodiments of the present invention, were performed by scanning electron microscopy. HRSEM micrographs were taken on a FEI Quanta 200 or on a high resolution SEM (Ziess Ultra-Plus FEG high resolution SEM, LEO 982, at different accelerating voltage between 4-20 kV). The sample was mounted on a carbon tab and sputter-coated with a thin layer of gold-palladium prior to SEM analysis. The average void size ($d_V$) was determined by manually measuring 50 to 100 voids in the SEM micrographs and applying a correction for the statistical nature of the fracture through a sphere (multiplying by $\frac{2}{3}^{1/2}$). The average window size ($d_{WN}$) was determined by manually measuring 50 to 100 windows in the SEM micrographs.

Colorant Scavenging:

The variation of methylene blue concentration with time was determined using UV spectroscopy (665 nm).

Example 2

Porosity

The composition-of-matter presented herein exhibits two types of pore populations that contribute to the total porosity of the structure ($P_{PH-T}$; total polyHIPE porosity), the porosity from the large spheroidal voids templated by the droplets of the organic dispersed phase of the HIPE ($P_{PH-V}$; void porosity) and the porosity within the hydrogel walls left after water was removed from pores within the polymer walls ($P_{PH-HG}$), which was calculated from the reference bulk hydrogel porosity ($P_{HG-T}$; total dry bulk hydrogel porosity).

$P_{PH-T}$, $P_{PH-HG}/P_{HG-T}$ and $P_{PH-V}$ were calculated using Equation 1, Equations 2a-b, and Equation 3, respectively, wherein $\rho_P$ denotes the density of the neat polymer (1.1 g/cm$^3$ as determined by helium pycnometry measurements of the N-70-y skeletal densities), $\rho_{PH}$ denotes the density of the dry polyHIPE, and $\rho_{HG}$ denotes the density of the bulk hydrogel.

$$P_{PH-T} = 1 - \frac{\rho_{PH}}{\rho_P} \quad \text{Equation 1}$$

$$P_{HG-T} = 1 - \frac{\rho_{HG}}{\rho_P} \quad \text{Equation 2a}$$

$$P_{PH-HG} = P_{HG-T}\left(\frac{\rho_{PH}}{\rho_{HG}}\right) \quad \text{Equation 2b}$$

$$P_{PH-V} = P_{PH-T} - P_{PH-HG} = 1 - \left(\frac{\rho_{PH}}{\rho_{HG}}\right) \quad \text{Equation 3}$$

Table 2A and Table 2B present various porosity properties of exemplary compositions-of-matter, according to some embodiments of the present invention, wherein $Y_p$ denotes yield of HIPE polymerization, $\rho_{PH}$ denotes the density of the dry polyHIPE, $P_{PH-T}$ denotes the total polyHIPE porosity, $P_{PH-V}$ denotes the porosity attributed to the spheroidal void, and $P_{HG-T}$ denotes the porosity of the wall/bulk hydrogel.

TABLE 2A

| Sample code | N-70-0.1 | N-70-0.5 | N-70-1 | N-70-5 | N-70-10 |
|---|---|---|---|---|---|
| $Y_p$ [%] | 75 | NA | 88 | 84 | 90 |
| $\rho_{PH}$ [g/cm$^3$] | 0.18 | 0.21 | 0.30 | 0.33 | 0.35 |
| $\rho_P$ | 1.1 | 1.1 | 1.099 | 1.095 | 0.939 |
| $P_{PH-T}$ [%] | 84 | 81 | 72 | 70 | 68 |
| $P_{PH-V}$ [%] | NA | NA | 61 | 62 | 57 |
| $P_{PH-HG}$ [%] | NA | NA | 11 | 8 | 11 |

TABLE 2B

| Sample code | N-85-0.1 | N-85-0.5 | N-85-1 | N-85-5 | N-85-10 |
|---|---|---|---|---|---|
| $Y_p$ [%] | 56 | 62 | 62 | 77 | 86 |
| $\rho_{PH}$ [g/cm$^3$] | 0.15 | 0.28 | 0.17 | 0.18 | 0.14 |
| $\rho_P$ | 1.1 | 1.1 | 0.885 | 0.789 | 0.892 |
| $P_{PH-T}$ [%] | 86 | 75 | 84 | 83 | 87 |
| $P_{PH-V}$ [%] | NA | NA | 78 | 79 | 83 |
| $P_{PH-HG}$ [%] | NA | NA | 6 | 4 | 4 |

The porosity of the composition-of-matter presented herein is dominated by the spheroidal voids and interconnecting windows. As can be seen in Table 2, $P_{PH-T}$ values for N-70-y are about 70% and the $P_{PH-V}$ are about 60%, indicating that the contribution of the voids dominates the porosity of the composition-of-matter. The same is seen for N-85-y with $P_{PH-T}$ values about 85% and $P_{PH-V}$ values of about 80%. The remainder of the porosity ($P_{PH-HG}$) is attributed to the pores left by water within the porous hydrogel walls. The polyHIPE densities, $\rho_{PH}$, were around 0.33 g/cm$^3$ for N-70-y and 0.16 g/cm$^3$ for N-85-y, as expected from their external phase contents of around 30% and 15%, respectively.

For comparison, the density and porosity of the corresponding reference bulk hydrogel were 0.77 g/cm$^3$ for R-1, 0.86 g/cm$^3$ for R-5, and 0.81 g/cm$^3$ for R-10. Table 3 presents other parameters of the reference bulk hydrogels, wherein $\rho_{HG}$ denotes the bulk hydrogel density, $P_{HG-T}$ denoted the porosity of the bulk hydrogel, $W_{HG-T}$ denotes the water uptake in the bulk hydrogel, and $S_{HG}$ denotes the equilibrium swelling ratios in water of the bulk hydrogel.

Table 3 presents densities, porosities, water-uptake and mechanical properties of various reference bulk hydrogels.

TABLE 3

| Sample codes | R-1 | R-5 | R-10 |
|---|---|---|---|
| $\rho_{HG}$ [g/cm] | 0.77 | 0.86 | 0.81 |
| $P_{HG-T}$ [%] | 30 | 22 | 26 |
| $W_{HG-T}$ [g/g] | 40 | 11 | 5 |

The porosity of the composition-of-matter presented herein, which is at least twice greater than the porosity of a corresponding reference bulk polymer/hydrogel, can explain the $W_{PH-T}$ that are higher than the equivalent $W_{HG-T}$ for MBAAm contents of 10%. However, the extraordinarily high $W_{PH-T}$ are more than 5 times the $W_{HG-T}$ for MBAAm contents of 1%, reaching 338 g/g for N-85-1.

Example 3

Water and Urine Uptake

The equilibrium water uptake ($W_U$ or $W_{PH-T}$), also referred to herein as the maximal absorption capacity, was determined by placing a sample cube (approximately 1 cm×1 cm×1 cm) with a known dry mass ($m_{Dry}$ or $m_D$) into a beaker filled with deionized water until a constant (equilibrium) swollen wet mass ($m_{Wet}$ or $m_{SW}$) was reached (at least 24 hours). The equilibrium water absorption (fully swollen) was calculated using Equation 6. The total uptake of water and urine were experimentally measured, while the components of water uptake were a model to support the void expansion theory.

The water and urine uptake by the composition-of-matter presented herein was determined by soaking the dry samples thereof in deionized water and artificial urine until swelling equilibrium was reached.

Artificial urine was prepared by dissolving 36.4 grams of urea in 1.5 liters of distilled water, and thereafter adding 15.0 grams of sodium chloride, 9.0 grams of potassium chloride and 9.6 grams of sodium phosphate thereto. The pH was adjusted to 6 by adding about 100 ml of 0.1 M NaOH. Specific gravity was measured by a urine hydrometer to be 1.017 g/ml.

There are three contributions to the total equilibrium water absorption ($W_{PH-T}$) of the presently provided composition-of-matter, first arising from the uptake within the original/dry void volume ($W_{PH-V}$), second arising from the uptake within the equilibrium swollen hydrogel walls ($W_{HG-T}$), and a third, dominant, uptake from hydrogel-swelling-driven void expansion ($W_{PH-VE}$). The ratio of the diameter of the swollen void to the diameter of the original void in the dry polyHIPE ($d_R$), was determined from measurements. Water uptake at equilibrium ($W_U$) was calculated using the wet mass ($m_{SW}$ or $m_{wet}$) of a swollen sample and the dry mass ($m_D$ or $m_{dry}$) of the same sample, cut into cubes of approximately 1 cm×1 cm×1 cm. Equilibrium was said to be reached after 24 hours of soaking, although it may be reached in a shorter period of time.

$$W_{PH-V} = P_{PH-V} \rho_W \quad \text{Equation 4}$$

$$W_{PH-VE} = W_{PH-T} - W_{PH-V} - W_{HG-T} \quad \text{Equation 5}$$

$$W_U = \left(\frac{m_{SW} - m_D}{m_D}\right) \quad \text{Equation 6}$$

Table 4A and Table 4B below present liquid absorption properties of exemplary compositions-of-matter according to some embodiments of the present invention, wherein $W_{PH-T}$ denotes the total water uptake by the composition-of-matter; $W_{PH-V}$ denotes the water uptake fraction in the dry void volume; $W_{HG-T}$ denotes the water uptake fraction by a corresponding reference bulk hydrogel; $W_{PH-VE}$ denotes the water uptake fraction from the void expansion and $U_{PH-T}$ denotes the total uptake of artificial urine by the composition-of-matter.

TABLE 4A

| Sample code | N-70-0.1 | N-70-0.5 | N-70-1 | N-70-5 | N-70-10 |
|---|---|---|---|---|---|
| $W_{PH-T}$ [g/g] | 977 | 473 | 270 | 27 | 13 |
| $W_{PH-V}$ [g/g] | NA | NA | 2.0 | 1.9 | 1.6 |
| $W_{HG-T}$ [g/g] | NA | NA | 40 | 11 | 5 |
| $W_{PH-VE}$ [g/g] | NA | NA | 228 | 14 | 6.4 |
| $U_{PH-T}$ [g/g] | 73 | 71 | 44 | 37 | 35 |

TABLE 4B

| Sample code | N-85-0.1 | N-58-0.5 | N-85-1 | N-85-5 | N-85-10 |
|---|---|---|---|---|---|
| $W_{PH-T}$ [g/g] | 755 | 613 | 338 | 168 | 31 |
| $W_{PH-V}$ [g/g] | NA | NA | 4.6 | 4.4 | 5.9 |
| $W_{HG-T}$ [g/g] | NA | NA | 40 | 11 | 5 |
| $W_{PH-VE}$ [g/g] | NA | NA | 293 | 153 | 20 |
| $U_{PH-T}$ [g/g] | 90 | 77 | 90 | 64 | 45 |

As can be seen in Table 4, the contribution of $W_{PH-VE}$ to the total water absorption increases with decreasing degree of crosslinking and with increasing porosity, and contributes over 84% to the total water absorption for the N-x-1. The contribution of $W_{PH-V}$ to the water uptake is minor, even for porosities of about 80-85%. $W_{HG-T}$ and $W_{PH-VE}$ are significantly larger than $W_{PH-V}$ and decrease with increasing crosslinking. As can further be seen in Table 4, the hydrogel-swelling-driven void expansion, expressed by $W_{PH-VE}$, notably dominates the water uptake at all crosslinking levels and particularly at the lowest degrees of crosslinking, reflecting the extensive structural expansion.

It seems that there is little influence of the extent of crosslinking on $W_{HG-T}$ or on $W_{PH-V}$. $W_{PH-V}$ is, however, significantly affected by the internal phase content, being around 1.8 and 5.0 g/g for N-70-y and N-85-y, respectively. This notable increase in $W_{PH-V}$ reflects the notable decrease in $\rho_{PH}$, from about 0.33 g cm$^{-3}$ for N-70-y to about 0.16 g cm$^{-3}$ for N-85-y, which indicates that, for a given volume, N-85-y contains about half the amount of polymer. $W_{PH-VE}$ is most strongly affected by the extent of crosslinking, but it is also significantly affected by the internal phase content. Increasing the extent of crosslinking restricts the ability of the composition-of-matter to swell and absorb water. The greater the internal phase content, the greater the effect of reducing the extent of crosslinking. Reducing the MBAAm content from N-x-10 to N-x-1 resulted in a 15-fold increase in $W_{PH-VE}$ for N-85-y and in a 36-fold increase for N-70-y. The extraordinarily high $W_{PH-T}$ for N-85-1, 338 g/g, originates in its extraordinary high $W_{PH-VE}$, 293 g/g, and from the relatively high $W_{HG-T}$, 40 g/g.

FIG. 1 presents photographs of an exemplary composition-of-matter, according to some embodiments of the present invention, N-85-y, showing the extensive change in dimensions of the sample upon equilibrium swelling, as a function of various degrees of crosslinking (y=10, 5 and 1, left to right).

FIGS. 2A-B present comparative plot of water uptake (FIG. 2A), and urine uptake (FIG. 2B), as a function of crosslinker level (0.1, 0.5, 1, 5 and 10 molar percent) on a logarithmic scale, as observed in exemplary compositions-of-matter, according to some embodiments of the present invention (N-70-y marked by squares and N-85-y marked by circles), their corresponding reference bulk hydrogels (marked by triangles), and a superabsorbent polymer used in commercial disposable household diapers (D1; dashed line).

As can be seen in FIGS. 2A-B, the $W_{PH-T}$ values of 270 and 338 g/g for N-70-1 and N-85-1, respectively, are somewhat higher than the water uptake observed in the commercial polymer, and more than 6 times higher than observed in the corresponding reference hydrogel. The $W_{PH-T}$ values for N-70-0.1 and N-85-0.1 are 977 and 755 g/g, respectively.

As can further be seen in FIGS. 2A-B, $W_{PH-T}$ values increased with decreasing degree of crosslinking for the compositions-of-matter presented herein, and their corresponding reference bulk hydrogel. Generally, $W_{PH-T}$ increases with increasing polyHIPE porosity reflecting the increase in pore volume, supporting the theory of a hydrogel-swelling-driven "void expansion" mechanism.

The measured ratio of the diameters of the swollen voids to those of the original voids in a dry composition-of-matter presented herein, was 2.2 for N-70-5 and 3.8 for N-85-5.

Similar to the water absorption, the artificial urine absorption generally increased with decreasing crosslinking and increased with increasing internal phase content. Unlike the water absorption, reducing the MBAAm content from N-x-10 to N-x-1 resulted in only a 2-fold increase in $W_{PH-VE}$ for N-85-y and in only 26% increase for N-70-y. Interestingly, $U_{PH-T}$ is significantly lower than $W_{PH-T}$ for N-x-1, as might be expected from the literature on sodium acrylate based superabsorbent hydrogels, but $U_{PH-T}$ is significantly higher than $W_{PH-T}$ for N-x-10. The lower absorbance of urine has been ascribed to the presence of the salts, which reduce osmotic swelling. Since this effect is most pronounced for N-70-10, it would seem that the phenomenon is related to a specific effect that the artificial urine has on the macromolecular nature of the AMPS/MBAAm hydrogel.

As can be seen in FIG. 2B, the results obtained for the uptake of artificial urine, $U_{PH-T}$, by the composition-of-matter presented herein, are similar to those observed with water uptake. $U_{PH-T}$ reached 90 g/g for N-85-0.1 and N-70-1, and the $U_{PH-T}$ valued for all compositions-of-matter were higher those observed in commercial diaper superabsorbent polymer. The combination of high porosity, the use of an ionic polymer, and a relatively low degree of crosslinking generated this extremely high superabsorbency.

Example 4

Microstructure

As discussed hereinabove, the monolithic porous composition-of-matter presented herein is HIPE-templated, namely its microstructure is a projection of the microstructure of a HIPE (or polyHIPE).

FIGS. 3A-F present SEM micrographs of exemplary dry compositions-of-matter, according to some embodiments of the present invention, wherein FIG. 3A is of dry N-70-1, FIG. 3B is of dry N-70-5, FIG. 3C is of dry N-70-10, FIG. 3D is of dry N-85-1, FIG. 3E is of dry N-85-5, and FIG. 3F is of dry N-85-10.

As can be seen in FIGS. 3A-F, the presently presented compositions-of-matter exhibit a highly interconnected, open-cell, porous microstructure that is typical of polyHIPEs, showing void diameters, $d_v$, in the 10 to 20 m range and windows diameters, $d_w$, in the 1 to 6 m range.

FIGS. 4A-D present SEM micrographs of exemplary compositions-of-matter, according to some embodiments of the present invention, wherein FIG. 4A shows the microstructure of a dry N-70-5 sample before it has been exposed to water, FIG. 4B shows the microstructure of a dry N-70-5 sample after equilibrium swelling in water, solvent exchange, and drying, FIG. 4C shows the microstructure of a dry N-85-5 sample before it has been exposed to water, and FIG. 4D shows the microstructure of a dry N-85-5 sample after equilibrium swelling in water, solvent exchange, and drying.

The swelling and the effects of swelling were evaluated following synthesis, Soxhlet extraction, and vacuum drying. As can be seen in FIGS. 4A-D, all the presently provided compositions-of-matter exhibit open-cell, highly interconnected, porous microstructure, templated by the microstructure of the polyHIPE. The effect of swelling on re-dried compositions-of-matter is shown in FIG. 4C and FIG. 4D for N-70-5 and N-85-5, respectively, wherein polyHIPE were prepared, washed and dried, and then swollen in water and vacuum dried again. Surprisingly, the interconnected porous microstructure typical of the composition-of-matter presented herein were fully preserved. The significant increases in the void and window diameters, in spite of the deswelling that invariably takes place during extraction and drying, incontrovertibly demonstrates that hydrogel-swelling-driven void expansion does take place. The diameter ratios taken from the SEM micrographs are about 2.2 for N-70-5 and about 3.8 for N-85-5.

Table 5 below presents various microstructure properties of exemplary compositions-of-matter according to some embodiments of the present invention, wherein $d_v$ denotes average spheroidal voids diameter (determined by SEM micrographs of dry samples); $d_w$ denotes average void-interconnecting "window" diameter (determined by SEM micrographs of dry samples); and $d_R$ denotes the ratio of the diameter of the swollen void to the diameter of the original void in the dry polyHIPE.

TABLE 5

| Sample code | N-70-1 | N-70-5 | N-70-10 | N-85-1 | N-85-5 | N-85-10 |
|---|---|---|---|---|---|---|
| $d_v$ [µm] | 22 ± 8 | 13 ± 5 | 11 ± 3 | 11 ± 3 | 10 ± 3 | 14 ± 6 |
| $d_w$ [µm] | 6 ± 4 | 5 ± 2 | 1.6 ± 0.8 | 1.0 ± 0.6 | 1.4 ± 1 | 2.4 ± 1 |

As can be seen in Table 5, the average void diameter, $d_v$, is in the 10 to 20 m range and the average windows diameter, $d_w$, is in the 1 to 6 m range.

It is noted that while the walls of the monolithic polymeric structures presented herein and shown in the SEM micrographs seem to be non-porous, they are in fact porous at a sub-micron level which is not visible at the magnification used to take the SEM micrographs. The sub-micrometric pores in the walls are left in place of water-filled pores which are present within every type of hydrogel, such as that constituting the walls of the presently described superabsorbent polymeric structures. Evidence to this level of porosity are found in the density measurements of the polymeric structures and their corresponding reference bulk hydrogels.

Example 5

Mechanical Properties

Compression is often used to describe and define foams and hydrogels. Compressive stress-strain tests were performed on either fully swollen or completely dry superabsorbent polyHIPE structures, as provided herein, or corresponding reference bulk hydrogels, at room temperature (using an Instron 3345). The samples were compressed until failure or until a strain of 70% was reached (a machine limitation).

The compressive modulus, E, is a substance's resistance to uniform compression as determined from the linear slope of a stress-strain curve at low strains. E reflects the initial stiffness or resistance to deformation of a substance.

A high E value means that the tested material changes its shape minimally when under stress, namely one needs to apply a higher stress in a high compressive modulus material, and a lower stress in a low compressive modulus material, in order to confer the same amount of deformation. Thus, high E values are desired in hydrogels used for most "structural" applications, especially for those that tend to lose water when deformed under stress.

$\varepsilon_F$ is the strain at which a sample of a material fails. It represents how much compressive strain can be applied to the material without causing a mechanically failure. For "stretching", a material with a high $\varepsilon_F$ can be pulled considerably without failing (rubber), while a material with a low $\varepsilon_F$ can only be "stretched" my a minimal amount (glass). Swollen hydrogels are often brittle and can fail at relatively low strains. Dry hydrogels are typically more brittle than wet (swollen) hydrogels. The strain at fail of a swollen hydrogel is denoted $\varepsilon_{F-SW}$ and given percent values, which mean that the swollen hydrogel can be compressed by an amount in percent of its original size before it fails. A higher $\varepsilon_{F-SW}$ value means a more durable (less brittle) superabsorbent material, which is a desirable feature for many applications.

$\sigma_F$ reflects the strength of a material, i.e., the stress at which the material undergoes catastrophic failure.

$\sigma_{70}$ is the stress at 70% strain (unidirectional deformation). It is used to compare foams and hydrogels that do not fail at 70% compressive strain, and is largely used to emphasize the fact that the materials have reached 70% strain without failing. Typically, when reaching 70% deformation, a foam/hydrogel material has collapsed, often after a "stress plateau" where the stress remains constant for a large strain range. The 70% value is chosen arbitrarily but is commonly used in the art. If a composition-of-matter, according to some embodiments of the present invention, is described using a $\sigma_{70}$ value, it typically means that it did not fail.

Table 6 below presents various mechanical properties of exemplary superabsorbent polymeric structures according to some embodiments of the present invention, wherein $E_{SW}$ denotes the modulus of the water-swollen structure; $E_D$ denotes the modulus of the dry structure; $\sigma_{F-SW}$ denotes stress at fail in the swollen state; $\varepsilon_{F-SW}$ denotes strain at fail in the swollen state; and $\sigma_{70-D}$ denotes stress at 70% compressive strain in the dry state.

TABLE 6

| Sample code | N-70-1 | N-70-5 | N-70-10 | N-85-1 | N-85-5 | N-85-10 |
|---|---|---|---|---|---|---|
| $\varepsilon_{F-SW}$ [%] | 51 | 66 | 66 | — | 60 | 69 |
| $E_{SW}$ [kPa] | 10 | 20 | 45 | — | 4.3 | 6.5 |
| $\sigma_{F-SW}$ [kPa] | 13 | 48 | 59 | — | 10 | 22 |
| $E_D$ [kPa] | 48000 | 70000 | 90000 | 900 | 1300 | 2400 |
| $\sigma_{70-D}$ [kPa] | 22946 | 30838 | 23833 | 780 | 420 | 610 |

Table 7 below presents various mechanical properties of reference bulk hydrogels corresponding to the compositions-of-matter presented in Table 6, wherein, $E_{SW}$ denotes modulus of the water-swollen hydrogel, $\sigma_{F-SW}$ denotes stress at fail, and $\varepsilon_{F-SW}$ denotes the strain at fail.

TABLE 7

| Sample codes | R-1 | R-5 | R-10 |
|---|---|---|---|
| $\varepsilon_{F-SW}$ [%] | 22.2 | 13.7 | 7.5 |
| $E_{SW}$ [kPa] | 350 | 1406 | 3209 |
| $\sigma_{F-SW}$ [kPa] | 105 | 193 | 261 |

Figures 5A, 5B:
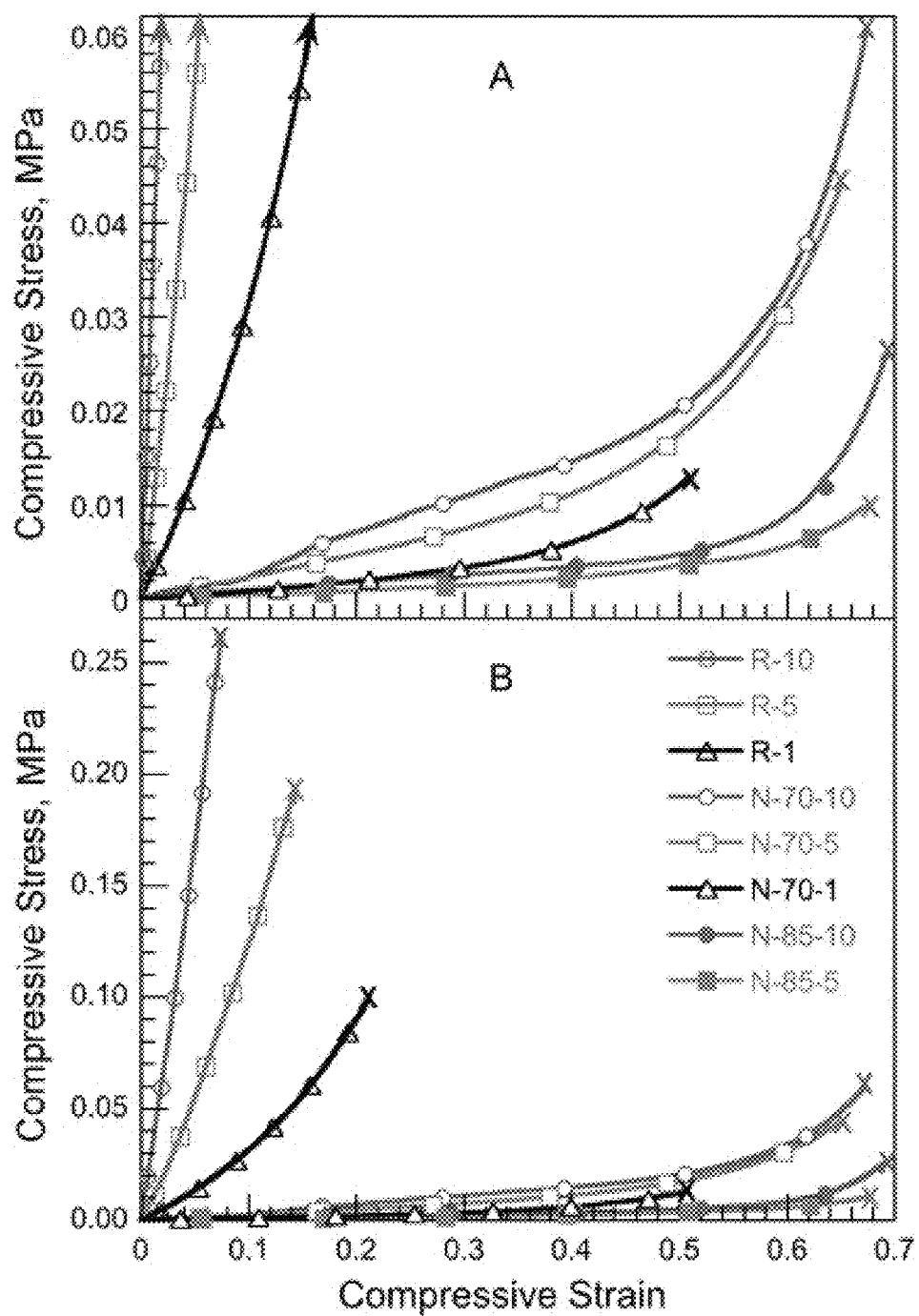

FIGS. 5A-B present the results of the compressive stress-strain studies conducted using fully swollen compositions-of-matter and corresponding reference bulk hydrogels, wherein FIG. 5A presents the results on a compressive stress scale of 0-0.062 MPa and FIG. 5B presents the results on a compressive stress scale of 0-0.27 MPa.

Figure 6A:
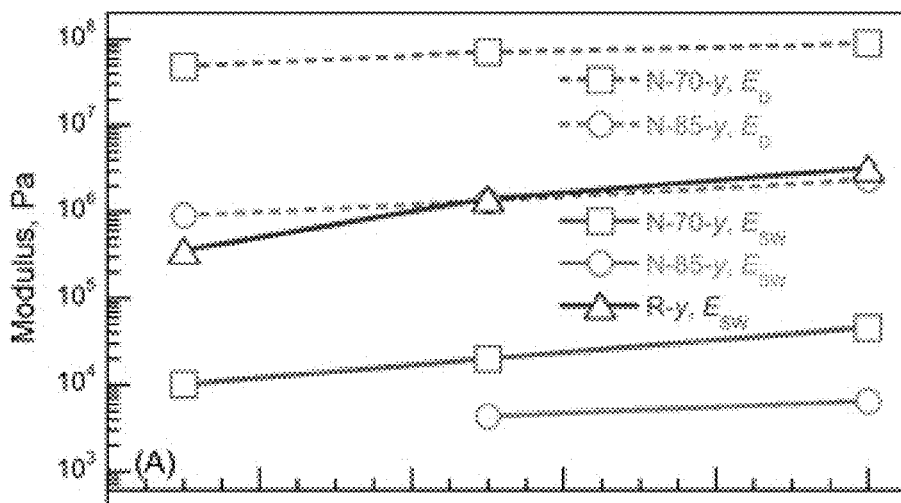
FIGS. 6A-C presents the results of the compressive stress-strain studies, showing the effect of the crosslinking co-monomer content on $E_{SW}$ (FIG. 6A), $\varepsilon_{F\text{-}SW}$ (FIG. 6B), and $\sigma_{F\text{-}SW}$ (FIG. 6C), for fully swollen compositions-of-matter and fully swollen corresponding reference bulk hydrogels, and of $E_D$ (FIG. 6A) and $\sigma_{70\text{-}D}$ (FIG. 6C), for the dry samples of compositions-of-matter, according to some embodiments of the present invention.
Figure 6B:
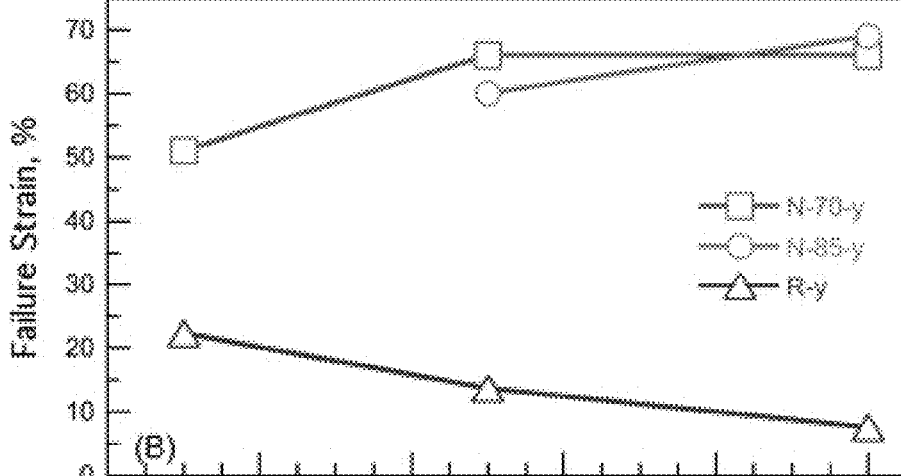
Figure 6C:
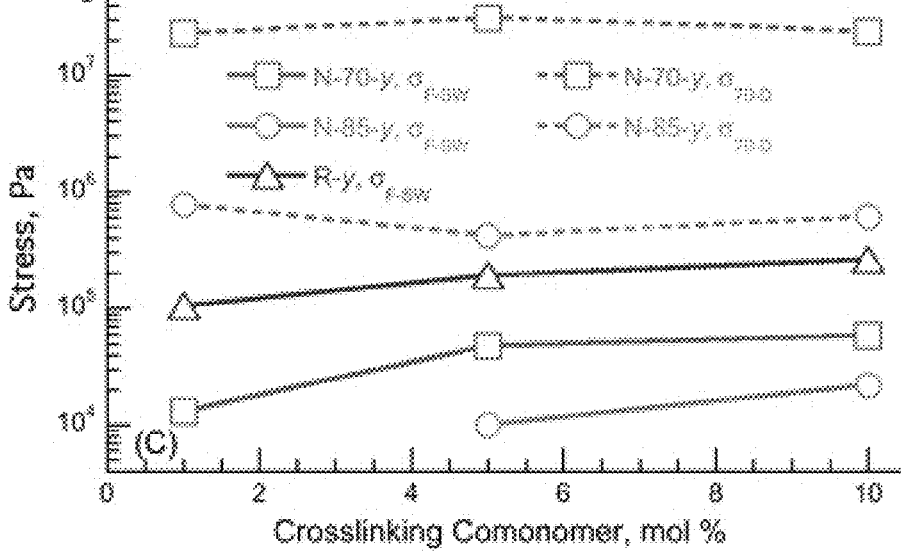

FIGS. 6A-C presents the results of the compressive stress-strain studies, showing the effect of the crosslinking co-monomer content on $E_{SW}$ (FIG. 6A), $\varepsilon_{F-SW}$ (FIG. 6B), and $\sigma_{F-SW}$ (FIG. 6C), for fully swollen compositions-of-matter and corresponding reference bulk hydrogels, and of $E_D$ (FIG. 6A) and $\sigma_{70-D}$ (FIG. 6C), for the dry samples of compositions-of-matter, according to some embodiments of the present invention.

As can be seen in Tables 6 and 7, and FIGS. 5A-B and 6A-C, there are significant differences in the compressive stress-strain characteristics of the water-swollen compositions-of-matter and their corresponding reference bulk hydrogels. The modulus, $E_{SW}$, increases with increasing crosslinking levels and increases with decreasing porosity. The significantly higher $E_{SW}$ of the reference bulk hydrogels reflect their significantly higher densities.

An extraordinary water retention for compressive strains reaching over 60% was observed. This phenomena is associated with the strong binding of water by the ionic polymer. While N-70-1 and N-70-5 do not retain all their water under compression, they reabsorb the water upon removal of the stress, reflecting preservation of structural features under strain. Most of the superabsorbent polymeric structures reach compressive strains larger than 60% without failing, and recover their shapes, about 97% of their original heights, upon removal of the stress.

As seen in FIG. 6B, the strains at fail, $\varepsilon_{F-SW}$, for most of these relatively flexible compositions-of-matter lie between 60-70%, while those of the corresponding reference bulk hydrogels are less than 22%. As seen in FIG. 6C, the stress at fail, $\sigma_{F-SW}$, increases with increasing crosslinking and with decreasing porosity, and the significantly higher $\sigma_{F-SW}$ reflect their significantly higher densities.

Figure 7A:
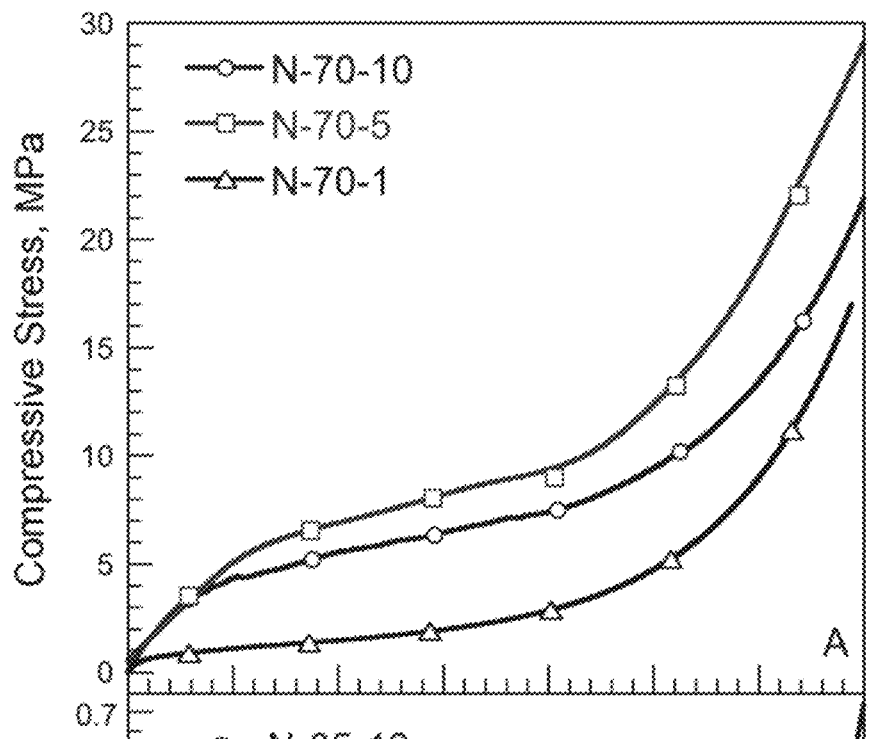
FIGS. 7A-B present the results of the compressive stress-strain studies conducted for the dry exemplary compositions-of-matter, N-70-y (FIG. 7A) and N-85-y (FIG. 7B), according to some examples of the present invention.
Figure 7B:
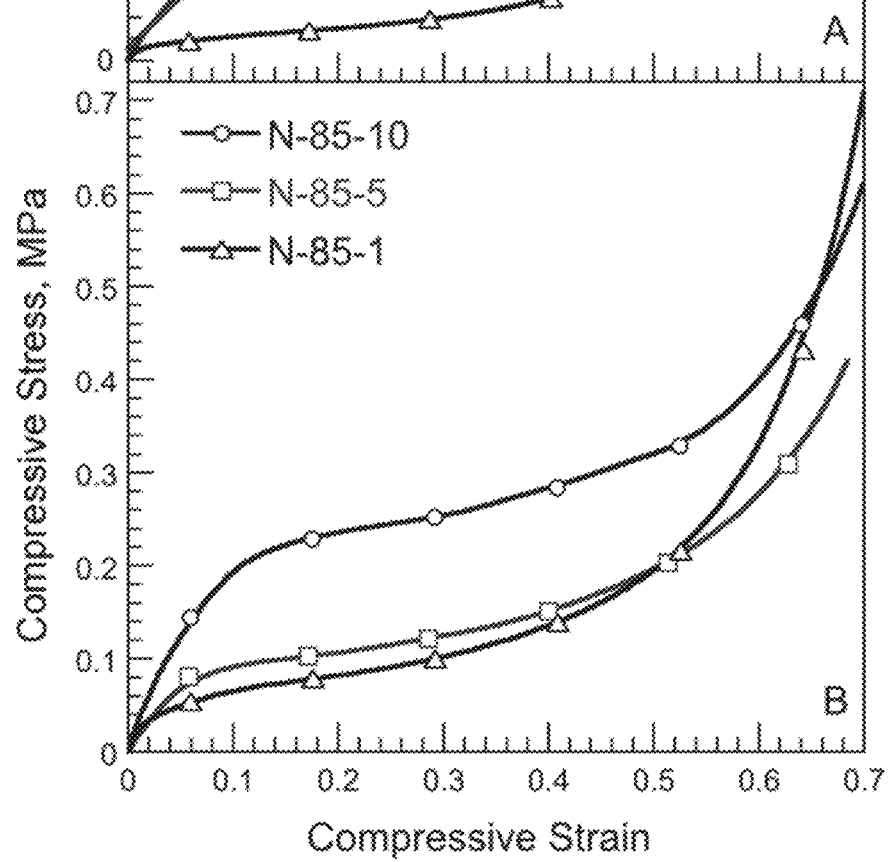

FIGS. 7A-B present the results of the compressive stress-strain studies conducted for the dry exemplary compositions-of-matter, N-70-y (FIG. 7A) and N-85-y (FIG. 7B), according to some examples of the present invention.

As can be seen in FIGS. 7A-B, the dry compositions-of-matter, according to some embodiments of the present invention, exhibit compressive stress-strain curves that are typical of dry foams, as opposed to wet hydrogels, namely a linear region at low strains, followed by a plateau region, and then a densification region characterized by a rapid increase in stress, reaching strains of 70% without failure. Unusually, the sample of dry N-70-y composition-of-matter exhibited extraordinarily high compressive moduli, $E_D$, between 50 and 90 MPa (FIG. 7A), which are comparable to those of polyHIPEs based on unusually stiff polymers such as dicyclopentadiene. The sample dry N-70-y composition-of-matter also exhibits extraordinarily high compressive stresses at 70% strain, $\sigma_{70-D}$, between 23-30 MPa (FIG. 6C), which are more than an order of magnitude larger than those in polystyrene-based polyHIPEs.

The modulus increases with increasing crosslinking and with decreasing porosity.

Example 6

Ion Exchange Capacity

The potential of using the presently provided composition-of-matter for ion exchange applications was demonstrated. The ion exchange capacity was determined by immersing cubic samples of exemplary compositions-of-matter, according to some embodiments of the present invention, having a mass that ranged from 1.0 to 1.5 grams, overnight in a beaker containing 100 mL of a 0.1 M aqueous solution of NaOH. The NaOH solution was then back-titrated with a 0.1 M aqueous solution of HCl using methyl orange as an indicator.

The number of sulfonate groups attached to the polymer chain was determined from the amount of HCl used in the back-titration.

The ion exchange capacity was calculated using Equation 7

$$IEC = \frac{(q_0 - q_e)}{m_D}$$ Equation 7 where $m_D$ is the mass of the dry composition-of-matter sample and $q_0$ and $q_e$ are the milliequivalents of NaOH before the titration and after an equilibrium was reached, respectively.

Samples of exemplary compositions-of-matter N-85-10 and N-70-10 exhibited ion exchange capacities of 7 and 8 meq NaOH per gram polymer (titrimetric analysis), respectively. It is noted that these values are more than twice the value of 3 meq NaOH per gram polymer for an aminated polystyrene-based polyHIPE as reported in the literature.

Example 7

Dye Absorption

The combination of sulfonic group accessibility and rapid capillary-action water absorption makes presently provided compositions-of-matter highly efficient dye absorbents. The potential of the presently provided compositions-of-matter for ion exchange applications was demonstrated using an experimental procedure involving samples of exemplary compositions-of-matter, according to some embodiments of the present invention, N-70-10 and N-85-10, to remove methylene blue (MB) from an aqueous solution.

N-70-10 and N-85-10 were used to scavenge MB from an aqueous solution containing 0.25 moles of MB per mole sulfonic acid groups. One gram samples of the polymeric structures were suspended in 250 mL of a 3 mmol/L aqueous solution of MB (0.78 mmol MB). The concentration of MB was dynamically determined using UV-Vis spectroscopy (UV-160 Shimadzu Spectrophotometer) at the characteristic wavelength of 665 nm. For each absorbance measurement, 2 mL of the MB solution was removed.

Figure 8:
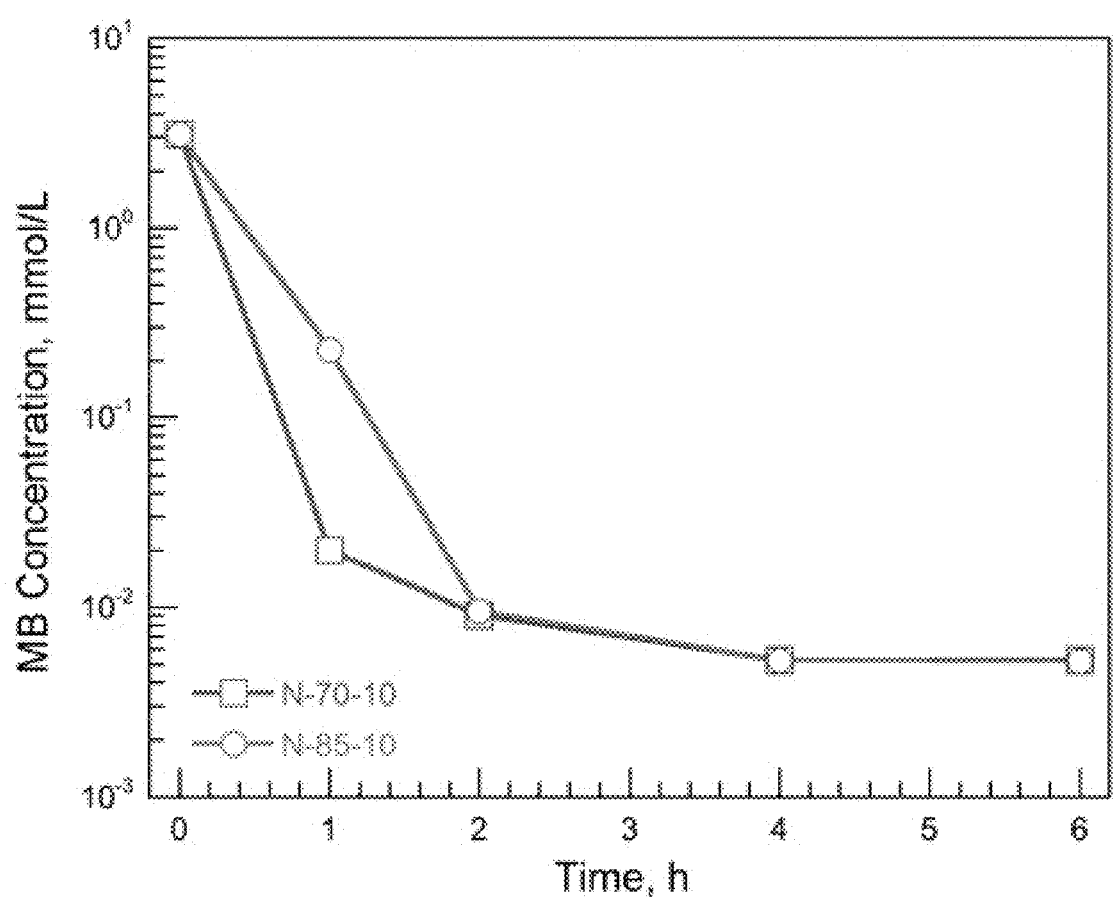
FIG. 8 presents the results of methylene blue scavenging, wherein the decrease in the methylene blue concentration is shown as a function of time.

FIG. 8 presents the results of methylene blue scavenging, wherein the decrease in the methylene blue concentration is shown as a function of time.

As can be seen in FIG. 8, methylene blue concentration decreased rapidly in the first hour, with approximately 98% of the MB removed after 4 hours.

The removal of almost all the dye from the water confirms that the highly accessible sulfonic acid groups in the compositions-of-matter provided herein make them promising dye absorption materials.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising a crosslinked polymer, the composition-of-matter having a microstructure of a polymerized external phase of a high internal phase emulsion and characterized by a dry density that ranges from 0.05 g/cm$^3$ to 0.4 g/cm$^3$, wherein:
   the composition-of-matter is derived from an oil-in-water emulsion which is a high internal phase emulsion that comprises an organic internal phase and an aqueous external phase;
   a crosslinking level of said crosslinked polymer ranges from 0.1 to 15 mol percent;
   said crosslinked polymer is having a plurality of pendant groups, at least a portion of which are ionizable pendant groups that are more strongly hydrated than a carboxylic pendant group;
   such that the composition-of-matter is characterized by:
   an equilibrium aqueous medium absorption of at least 8 g/g; and
   a compressive failure strain of at least 25% when the composition-of-matter is fully swollen with said aqueous medium.

2. The composition-of-matter of claim 1, wherein said compressive failure strain of the composition-of-matter is at least 2-fold greater than a compressive failure strain of a reference bulk hydrogel made with said crosslinked polymer but not prepared as an external phase of a high internal phase emulsion.

3. The composition-of-matter of claim 1, wherein a ratio of said ionizable pendant groups to non-ionizable pendant groups in said crosslinked polymer is greater than 85 percent.

4. The composition-of-matter of claim 1, wherein said polymer is substantially devoid of non-ionizable pendant groups.

5. The composition-of-matter of claim 1, wherein said ionizable pendant groups comprise at least one organosulfur group.

6. The composition-of-matter of claim 1, wherein said microstructure is an open-cell microstructure.

7. The composition-of-matter of claim 1, wherein said crosslinked polymer comprises poly(2-acrylamido-2-methylpropanesulfonic acid).

8. The composition-of-matter of claim 1, wherein said crosslinked polymer is crosslinked with N,N'-methylenebisacrylamide (MBAAm).

9. The composition-of-matter of claim 8, wherein said crosslinking level ranges from 0.1 to 5 mol percent and said dry density is 0.15 g/cm$^3$.

10. The composition-of-matter of claim 8, wherein said crosslinking level ranges from 0.1 to 5 mol percent and said dry density is 0.30 g/cm$^3$.

11. The composition-of-matter of claim 1, wherein said aqueous external phase is a pre-polymerization mixture that comprises a plurality of monomers and crosslinking agents, wherein a mol percent of said crosslinking agents in said plurality of monomers and crosslinking agents ranges from 0.5 percent to 15 percent, and said organic internal phase constitutes from 60 percent to 95 percent of said high internal phase emulsion.

12. The composition-of-matter of claim 11, wherein at least 85 percent of said plurality of monomers are ionizable monomers.

13. The composition-of-matter of claim 12, wherein said ionizable monomers are selected from the group consisting of 2-acrylamido-2-methylpropane sulfonic acid (AMPS), 2-acrylamido-2-propanesulfonic acid, 1-acrylamido-1-propanesulfonic acid, 2-(methacryloyloxy)ethanesulfonic acid, 2-hydroxy-3-(2-propenyloxy)-propanesulfonic acid, 2-methacrylamido-2-methyl-1-propanesulfonic acid, 2-methyl-2-propene-1-sulfonic acid, 2-propene-1-sulfonic acid, 2-sulfoethyl acrylate, 2-sulfoethyl methacrylate, 3-methacrylamido-2-hydroxypropanesulfonic acid, 3-sulfopropyl acrylate, 3-sulfopropyl methacrylate, 3-sulfopropylacrylate, 3-sulfopropylmethacryflate, allyl sulfonic acid, allyloxybenzenesulfonic acid, methallyloxybenzenesulfonic acid, methallylsulfonic acid, phenylethenesulfonic acid, styrenesulfonic acid, sulfomethacrylamide, sulfomethylmethacrylamide, vinylsulfonic acid, and any salts thereof, and any combinations thereof.

14. The composition-of-matter of claim 11, wherein said crosslinking agent is selected from the group consisting of N,N'-methylenebisacrylamide (MBAAm) ethylene glycol diacrylate, diethylene glycol diacrylate, N-(1-hydroxy-2,2-dimethoxyethyl)acrylamide, N,N'-(1,2-dihydroxyethylene) bisacrylamide, and any combination thereof.

15. The composition-of-matter of claim 11, wherein said high internal phase emulsion further comprises a surfactant and an initiator.

16. The composition-of-matter of claim 15, wherein said surfactant is a hydrophilic non-ionic surfactant.

17. A hydrogel comprising the composition-of-matter of claim 1, and an aqueous medium absorbed therein.

18. The hydrogel of claim 17, wherein said aqueous medium is selected from the group consisting of water, a solution of a water-soluble substance, waste-water, and urine.

19. An article of manufacture comprising the composition-of-matter of claim 1.

20. The article of claim 19, selected from the group consisting of a diaper, an incontinence garment, a fire-retardant material, a flood or spill control device, a fragrance carrier, a thermal pack, a liquid waste device, an ion-exchange matrix, a filter matrix, a water purification matrix, a surgical pad, a water retention device, a cosmetic product, a personal hygiene product, a personal care product, a grooming product and a wound dressing.

* * * * *